US008440709B2

(12) United States Patent  
Zamir

(10) Patent No.: US 8,440,709 B2  
(45) Date of Patent: May 14, 2013

(54) POLYMORPHS AND AMORPHOUS FORMS OF 5-AMINO-1-[2,6-DICHLORO-4-(TRIFLUORO METHYL)PHENYL]-4-[(TRIFLUORO METHYL)SULFINYL]-1H-PYRAZOLE-3-CARBONITRILE

(75) Inventor: Sharona Zamir, Omer (IL)

(73) Assignee: Makhteshim Chemical Works Ltd., Beer Sheva (IL)

(*) Notice: Subject to any disclaimer, the term of this patent is extended or adjusted under 35 U.S.C. 154(b) by 720 days.

(21) Appl. No.: 12/097,615

(22) PCT Filed: Dec. 14, 2006

(86) PCT No.: PCT/IL2006/001441  
§ 371 (c)(1),  
(2), (4) Date: Dec. 2, 2008

(87) PCT Pub. No.: WO2007/069254  
PCT Pub. Date: Jun. 21, 2007

(65) Prior Publication Data  
US 2009/0093532 A1    Apr. 9, 2009

Related U.S. Application Data

(60) Provisional application No. 60/750,046, filed on Dec. 14, 2005.

(30) Foreign Application Priority Data

Dec. 14, 2005  (IL) .......................................... 172585

(51) Int. Cl.  
*A61K 31/415* (2006.01)  
*C07D 231/00* (2006.01)

(52) U.S. Cl.  
USPC ....................................... 514/407; 548/371.4

(58) Field of Classification Search .................. 514/407; 548/371.4  
See application file for complete search history.

(56) References Cited

U.S. PATENT DOCUMENTS

| | | | |
|---|---|---|---|
| 5,082,945 A | | 1/1992 | Wakselman et al. |
| 5,160,530 A | | 11/1992 | Misselbrook et al. |
| 5,232,940 A | * | 8/1993 | Hatton et al. ................ 514/407 |
| 5,618,945 A | | 4/1997 | Casado et al. |
| 5,631,381 A | | 5/1997 | Huang et al. |
| 6,346,542 B1 | | 2/2002 | Huber |

FOREIGN PATENT DOCUMENTS

| | | |
|---|---|---|
| CN | 1374298 A | 10/2002 |
| EP | 0 295 117 A1 | 12/1988 |
| EP | 0 374 061 | 6/1990 |
| EP | 0 460 940 | 12/1991 |
| EP | 0 484 165 | 5/1992 |
| EP | 0 668 269 | 8/1995 |
| EP | 0 967 206 | 12/1999 |
| EP | 1 331 222 | 7/2003 |
| WO | 93/06089 | 4/1993 |
| WO | 00/62616 | 10/2000 |
| WO | 01/30760 | 5/2001 |
| WO | 01/30760 A1 | 5/2001 |
| WO | 2005/060749 A1 | 7/2005 |
| WO | 2005/095349 A1 | 10/2005 |
| WO | 2007/069254 | 6/2007 |
| WO | 2007069254 A3 | 6/2007 |
| WO | 2007122440 | 11/2007 |
| WO | 2008/055881 A1 | 5/2008 |
| WO | 2008/055882 A1 | 5/2008 |
| WO | 2008/055883 A1 | 5/2008 |
| WO | 2008/055884 A1 | 5/2008 |
| WO | 2012/007938 | 1/2012 |
| WO | 2012/095871 A2 | 7/2012 |
| WO | 2012/095871 A3 | 7/2012 |

OTHER PUBLICATIONS

Brittain's, 1999, pp. 348-361.*  
Caira, "Crystalline polymorphism of Organic Compounds", Topics in Current Chemistry 198: 163-208 (1998).  
Braga et al, "Chapter 8: Polymorphism, Crystal Transformations and Gas-Solid Reactions", Crystal Design: Structure and Function, vol. 7, pp. 325-373, ISBN 0-470-84333-0 (2003).  
Braga et al, "Crystal Polymorphism and multiple crystal forms", Struct Bond 132, pp. 25-50 (2009).  
Braga et al, "Making crystals from crystals: a green route to crystal engineering and polymorphism", Chem. Commun, pp. 3635-3645 (2005).  
Van Tonder et al "Preparation and Physicochemical Characterization of 5 Niclosamide Solvates and 1 Hemisolvate", AAPS PharmSciTech, 5(1): 1-10 (2004).  
Nangia et al "Pseudopolymorphism: occurrences of hydrogen bonding organic solvents in molecular crystals", Chem. Commun., pp. 605-606 (1999).  
Laird, "Editorial: Polymorphism—Still Unpredictable?", Organic Process Research & Development, 14(1) (2010).  
Fipronil (±)-5-amino-1-(2,6 dichloro-α,α,α-trifluoro-p-tolyl)-4-trifluoromdthlsupphiny pyrazole-3-carbonitrile AGP: CP/363, 1998.  
International Preliminary Report on Patentability issued in PCT/IL06/01441 on Mar. 10, 2009 (6 pages).  
Written Opinion issued in PCT/IL06/01441 on Oct. 16, 2008 (5 pages).  
Fipronil (354), The e-pesticide Manual (Thirteenth Edition) British Crop Protection Council, XP002485045, copyright 2003 (2 pages).  
European partial Extended Supplementary Search Report (ESSR) along with European Search Opinion issued in corresponding EP application 06 832 241.1 on Jan. 26, 2011 (11 pages).  
Third party observations filed in corresponding EP application 06 832 241.1 on Nov. 4, 2008 (21 pages).

(Continued)

*Primary Examiner* — Rei-tsang Shiao  
(74) *Attorney, Agent, or Firm* — Browdy and Neimark, PLLC

(57) ABSTRACT

The present invention relates to novel crystalline polymorphs, solvate pseudomorphs and amorphous form of 5-amino-1-[2,6-dichloro-4-(trifluoromethyl)phenyl]-4-[(trifluoromethyl)sulfinyl]-1H-pyrazole-3-carbonitrile (fipronil). The present invention also provides methods for preparing the novel polymorphs, pseudomorphs and amorphous form, as well as insecticidal or pesticidal compositions comprising same, and methods of use thereof as pesticidal agents.

17 Claims, 15 Drawing Sheets

OTHER PUBLICATIONS

Official Action issued by the Canadian Patent Office on Mar. 16, 2011, in Canadian Patent Appln No. 2,630,849.

Gu et al, "Polymorph Screening: Influence of Solvents on the Rate of Solvent-Mediated Polymorphic Transformation," Journal of Pharmaceutical Sciences, 90(11): 1878-1890 (2001).

Rustichelli et al, "Solid-state study of polymorphic drugs: carbamazepine," Journal of Pharmaceutical and Biomedical Analysis, 23: 41-54 (2000).

Stahly, "Diversity in Single- and Multiple-Component Crystals. The Search for and Prevalence of Polymorphs and Cocrystals," Crystal Growth & Design, 7(6): 1007-1026 (2007).

Haleblian et al, "Pharmaceutical Applications of Polymorphism," Journal of Pharmaceutical Sciences 58(8): 911-929 (Aug. 1969).

"The effect of *Metarhizium anisopliae* (Metsch)Sorokin (=flavoviride) Gams and Rozsypal var. acridum (Deuteromycotina: Hypomycetes) on non-target Hymenoptera", von Ine Stolz, Basel (1999) pp. 8-9.

Environmental fate of Fipronil; Pete Connelly (Dec. 2001) pp. 2-3, 4, 11.

Caracterisation des risques induits par les activites agricoles sur les ecosystems aquatiques (Devez) especially p. 11 (English translation submitted), Jul. 23, 2004.

Brittain,H.G., Preparation and Identification of Polymorphs and Solvatomorph "Preformulation in Solid Dosage Form Development," pp. 185-228 (5th ed., M.C. Adeyeye et al., eds. (2008).

Brittain and Fiese, Effects of Pharmaceutical Processing, pp. 348-361 (1999).

Guillory, J.K., "Generation of polymorphs, hydrates, solvates, and amorphous solids" Polymorphism in Pharmaceutical Solids (H.G. Brittain ed.) pp. 183-220 (1999).

Morrissette, S.L. et al, Advanced drug delivery reviews, vol. 56, pp. 275-300 (2004).

Desikan, et al "Process development challenges to accommodate a late-appearing stable polymorph: a case study on the polymorphism and crystallization of a fast-track drug development compound," Org. Process Res. Dev., vol. 9, pp. 933-942 (2005).

Roy et al "Crystal Polymorphism: Unmasking a third polymorph of a benchmark crystal-structure-prediction compound" Angew. Chem., Int. Ed. 2009, vol. 48, 8505-8508 (2009).

Yang et al "Study on Synthesis of Fipronil" J. of Heibei University of Science and Technology, vol. 25 (2), Sum 69 (2004), Dok. Serial No. 1008-1542 (2004) 02-0018-03 (six pages).

Official Action issued in copending Japanese patent application JP 2008-545252 dated Jul. 24, 2012 (English-language translation, three pages).

Lin et at "Nongyao: Synthesis of the New Insecticide—Fipronil", Agricultural Chemicals, vol. 41, Issue 3, p. 19. (2002) (six pages).

Schott, Hans, "Colloidal Dispersions", Remington: Practice of the Science and Pharmacy, 19th Ed. Chapter 20, Mack Publishing, Easton PA, pp. 252-277 (1995).

Radebaugh Galen W. and Ravin, Louis J., "Preformulation", Remington: Practice of the Science and Pharmacy, 19th Ed. Chapter 83, Mack Publishing, Easton PA, pp. 1447-1462 (1995).

O'Connor, Robert E., et al., "Powders", Remington: Practice of the Science and Pharmacy, 19th Ed. Chapter 91, Mack Publishing, Easton PA, pp. 1598-1614 (1995).

Tang et al Acta Crystallographica, Section E: Structure reports online, vol. E61, No. 12, pp. 04374-04375 (2005).

Cabri et al, "Polymorphisms and Patent, Market, and Legal Battles: Cefdinir Case Study," Organic Process Research & Development 11: 64-72 (2007).

Papathoma, "Patenting Polymorphs at the European Patent Office," Barcelona, 28 pages, Jun. 19-21, 2006.

Liebenberg, "Crystal Polymorphism and it Occurance Among Active Pharmaceutical Ingredients in South Africa" North West Univerisity, 29 pages (2005).

Newman, et al, "Solid-state analysis of the active pharmaceutical ingredient in drug products," Drug Discovery Today, 8(19): 898-905 (Oct. 2003).

Jain et al, "Polymorphism in Pharmacy" Indian drugs, 23(6): 315-329 (1986).

* cited by examiner

POLYMORPHS AND AMORPHOUS FORMS OF 5-AMINO-1-[2,6-DICHLORO-4-(TRIFLUORO METHYL)PHENYL]-4-[(TRIFLUOROMETHYL) SULFINYL]-1H-PYRAZOLE-3-CARBONITRILE

FIELD OF THE INVENTION

The present invention relates to novel crystalline and amorphous forms of 5-amino-1-[2,6-dichloro-4-(trifluoromethyl) phenyl]-4-[(trifluoromethyl)sulfinyl]-1H-pyrazole-3-carbonitrile (fipronil), to processes for their preparation, compositions comprising the new forms, and their use as pesticidal agents.

BACKGROUND OF THE INVENTION

It is known from inter alia, EP-A-0 295 117 and U.S. Pat. No. 5,232,940, that certain N-phenylpyrazole compounds are useful for the control of arthropod, plant nematode, helminth and protozoan pests. These compounds include N-phenylpyrazoles having an optionally substituted amino group attached to the 5-position. Such substituted amino groups include amino substituted by one or two groups selected from alkyl and alkanoyl. Compounds of interest include those having a cyano group attached to the 3-position and a group $RS(O)_n$ attached to the 4-position, R being selected from alkyl and haloalkyl and n being 0, 1 or 2.

Among the compounds in the above-mentioned publications is listed 5-amino-3-cyano-1-(2,6-dichloro-4-trifluoromethylphenyl)-4-trifluoromethyl sulfinylpyrazole, which is depicted as the following formula:

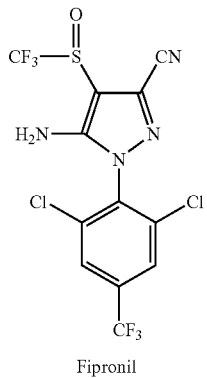 [SMILES: N#Cc1nn(-c2c(Cl)cc(C(F)(F)F)cc2Cl)c(N)c1S(=O)C(F)(F)F]

Fipronil

This compound is currently used commercially to control pests in, for example, agriculture, public health and animal health, and is known as fipronil. Fipronil is a broad spectrum insecticide, toxic by contact and ingestion. It is used to control multiple species of thrips on a broad range of crops by foliar, soil or seed treatment, control of corn rootworm, wireworms and termites by soil treatment in maize and control of boll weevil and plant bugs on cotton, diamond-back moth on crucifers, Colorado potato beetle on potatoes by foliar application. It is also widely used in household pest control including roach and ant control and as a termiticide, as well as for treatment of household pets or other animals.

There is an urgent and unmet need in the art for efficient methods for the preparation and purification of fipronil, which are simple and can be used on a large scale for industrial manufacture, and which produce highly pure product that can be safely utilized.

SUMMARY OF THE INVENTION

The present invention relates to novel crystalline polymorphs, solvate pseudomorphs and an amorphous form of 5-amino-1-[2,6-dichloro-4-(trifluoromethyl)phenyl]-4-[(trifluoromethyl)sulfinyl]-1H-pyrazole-3-carbonitrile (fipronil). The present invention also provides methods for preparing the novel polymorphs, pseudomorphs and amorphous form, as well as pesticidal or insecticidal compositions comprising same, and methods of use as pesticidal and insecticidal agents.

In one embodiment, the present invention provides a novel crystalline polymorphic form of fipronil, designated "Form I". Form I exhibits an X-ray powder diffraction pattern substantially as shown in FIG. 1, having characteristic peaks (expressed in degrees 2θ (+/−0.2°θ) at one or more of the following positions: 10.3, 11.05, 13.04, 15.93, 16.27, 18.48, 19.65, 20.34, 22.05, and 31.55. Form I also exhibits an infrared (IR) spectrum at the 3000 $cm^{-1}$ range substantially as shown in FIG. 2, having characteristic peaks at about 3332 and 3456. Form I also exhibits a Differential Scanning Calorimetry (DSC) thermogram substantially as shown in FIG. 3, which is characterized by a predominant endotherm peak at about 202.5° C. as measured by Differential Scanning Calorimeter at a scan rate of 2° C. and/or 10° C. per minute.

In another embodiment, the present invention provides a novel crystalline polymorphic form of fipronil designated "Form II". Form II exhibits an X-ray powder diffraction pattern substantially as shown in FIG. 4, having characteristic peaks (expressed in degrees 2θ (+/−0.2°θ) at one or more of the following positions: 11.7, 14.4, 15.7, 16.75, 17.2, 18.2, 19, 20.7, 22.95, 23.55, and 2.0. Form II also exhibits IR spectrum at the 3000 $cm^{-1}$ range substantially as shown in FIG. 5, having characteristic peaks at about 3344 and 3436.5 $cm^{-1}$. Form II also exhibits a DSC thermogram substantially as shown in FIG. 6, which is characterized by a predominant endotherm at about 195° C., as measured by Differential Scanning Calorimeter at a scan rate of 2° C. and/or 10° C. per minute.

In another embodiment, the present invention provides a novel crystalline polymorphic form of fipronil, designated "Form III". Form III exhibits an X-ray powder diffraction pattern substantially as shown in FIG. 7, having characteristic peaks (expressed in degrees 2θ (+/−0.2°θ) at one or more of the following positions: 15.6, 16.7, 17.1, 27.2, and 31.9. The DSC of fipronil toluene hemi solvate pseudomorph (FS-T) at a scan rate of 10° C. per minute (FIG. 8) shows an endothennic transformation of FS-T to Form III at ~110° C. and the exothermic transformation of form III to form I at 150° C.

In another embodiment, the present invention provides a novel toluene hemi solvate pseudomorph of fipronil, designated "FS-T". The FS-T pseudomorph exhibits an X-ray powder diffraction pattern substantially as shown in FIG. 10, having characteristic peaks (expressed in degrees 2θ (+/− 0.2°θ) at one or more of the following positions: 7.2, 9.3, 12.5, 15.1, 18.65, 19.15, 20.85, 25.95, 28.1, 30.05, and 33.40. Pseudomorph FS-T also exhibits an IR spectrum at the 3000 $cm^{-1}$ range substantially as shown in FIG. 11, having characteristic peaks at about 694.6 and 733.2 $cm^{-1}$ (toluene solvent); and 3328.4 and 3409.5 $cm^{-1}$ ($NH_2$ asymmetric and symmetric stretches). Upon stepwise heating to 150° C. and cooling to 60° C., fipronil FS-T converts to Form I, as shown in FIG. 9.

In another embodiment, the present invention provides a novel methyl isobutyl ketone (MIBK) hemi solvate pseudomorph of fipronil, designated "FS-M". The FS-M pseudomorph exhibits an X-ray powder diffraction pattern substantially as shown in FIG. 12, having characteristic peaks (expressed in degrees 2θ (+/−0.2°θ) at one or more of the following positions: 6.6, 8.15, 11.85, 19.95, 20.45, 23.10, 26.6, 28.8, and 31.30. Pseudomorph FS-T also exhibits an IR spectrum at the 3000 cm$^{-1}$ range substantially as shown in FIG. 13, having characteristic peaks at about 1710 cm$^{-1}$ (MIBK ketone); and 3409.5 and 3328 cm$^{-1}$ (NH$_2$ asymmetric and symmetric stretches). Pseudomorph FS-M also exhibits DSC thermogram embedded with TGA (Thermal Gravimetric Analysis) thermogram substantially as shown in FIG. 14.

In another embodiment, the present invention provides a novel amorphous fipronil, which exhibits an X-ray powder diffraction pattern substantially as shown in FIG. 15.

In another embodiment, the present invention provides a mixture of polymorphic Form I and Form II of 5-amino-1-[2,6-dichloro-4-(trifluoromethyl)phenyl]-4-[(trifluoromethyl)sulfinyl]-1H-pyrazole-3-carbonitrile (fipronil). Preferably, the mixture comprises from about 10% to about 90% by weight of fipronil Form I, and from about 90% to about 10% by weight fipronil Form II.

In another aspect, the present invention provides processes for preparing the novel polymorphs of fipronil Form I, Form II, Form III, the novel pseudomorphs FS-T and FS-M, and amorphous fipronil.

In one embodiment, Form I fipronil can be prepared by heating a fipronil pseudomorph FS-T to a temperature greater than about 100° C., preferably a temperature of about 150° C., cooling, and isolating the product. Preferably, the process further comprises grinding the pseudomorph FS-T, before, after or during the heating step. An intermediate in the conversion of pseudomorph FS-T to Form I is a novel polymorphic fipronil Form III. As a result of heating FS-T, solvent liberation occurs resulting in the formation of Form III, which then undergoes exothermic transition to Form I.

In one embodiment, Form II fipronil can be prepared by crystallizing fipronil from a solvent selected from the group consisting of isopropyl alcohol, hexane, ethyl acetate, 1-propanol, butanol, and MIBK, or any mixture of these solvents; and isolating the resulting crystals. In a currently preferred embodiment, the process includes preparing a solution of the compound in one or more of the aforementioned solvents, preferably by applying heat until dissolution is complete, cooling the solution until crystals appear (typically 0° C. to room temperature), and isolating the crystals. In one embodiment, the crystallization solvent is isopropyl alcohol. In another embodiment, the crystallization solvent is a mixture of ethyl acetate and n-hexane. In yet another embodiment, the crystallization solvent is a mixture of n-hexane and MIBK. When a solvent mixture is used, fipronil can be dissolved in one solvent followed by the addition of the other, in any order, or fipronil can be simultaneously dissolved in the solvent mixture.

In one embodiment, pseudomorph FS-T fipronil can be prepared by crystallizing fipronil from toluene. In a currently preferred embodiment, the process includes preparing a solution of the compound is toluene, preferably by applying heat until dissolution is complete, cooling the solution until crystals appear (typically 0° C. to room temperature), and isolating the crystals.

In one embodiment, pseudomorph FS-M fipronil can be prepared by crystallizing fipronil from MIBK and n-hexane. Generally, fipronil is dissolved in MIBK and n-hexane (either simultaneously or sequentially), preferably with heat, and the flask is left to stand in the air so that the solvent slowly evaporates. Gradually, crystals begin to appear, which are then isolated.

In one embodiment, amorphous fipronil is prepared by heating fipronil to a temperature greater than its melting point (preferably to a temperature greater than about 202.5° C., more preferably to a temperature of about 215° C.), and cooling.

In another aspect, the present invention provides pesticidal compositions comprising the novel crystalline polymorphs, solvate pseudomorphs and/or the novel amorphous fipronil, which are useful for controlling pests. In one embodiment, the compositions comprise a pesticidally effective amount of crystalline polymorph Form I fipronil; and an acceptable adjuvant. In another embodiment, the composition comprises a pesticidally effective amount of crystalline polymorph Form II of fipronil; and an acceptable adjuvant. In another embodiment, the composition comprises a pesticidally effective amount of crystalline polymorph Form III of fipronil; and an acceptable adjuvant. In yet another embodiment, the composition comprises a pesticidally effective amount of pseudomorph FS-T of fipronil; and an acceptable adjuvant. In yet another embodiment, the composition comprises a pesticidally effective amount of pseudomorph FS-M of fipronil; and an acceptable adjuvant. In yet another embodiment, the composition comprises a pesticidally effective amount of an amorphous fipronil; and an acceptable adjuvant. The compositions of the present invention are preferably intended for use in veterinary medicine, and can be administered by any method known in the art.

The present invention also relates to methods for controlling pests at a locus, comprising applying to the locus a pesticidally effective amount of a composition of the present invention. In some embodiments the locus is an agricultural locus, including but not limited to agricultural crops and fields. In some embodiments the locus is a structure, including but not limited to residential premises, commercial premises or farmyard structures. In some embodiments the locus is an animal, including wild animals treated to prevent insect borne diseases, as well as a domestic animal or a household pet including but not limited to a dog or a cat. In one preferred embodiment, the composition is administered topically or by spraying. In some embodiments the composition is administered in the form of gels, granules or as bait for pests.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The present invention is generally directed to novel crystalline polymorphic forms of 5-amino-1-[2,6-dichloro-4-(trifluoromethyl)phenyl]-4-[(trifluoromethyl) sulfinyl]-1H-pyrazole-3-carbonitrile (fipronil) referred to herein as "polymorph Form I", "polymorph Form II", and "polymorph Form III". The invention is further directed to novel solvate pseudomorphs of fipronil, specifically a toluene hemi-solvate designated herein "pseudomorph FS-T", and a methyl isobutyl ketone (MIBK) hemi-solvate designated herein "pseudomorph FS-M". The invention is further directed to a novel amorphous form of fipronil. The present invention also provides methods for preparing the novel polymorphs, pseudomorphs and amorphous form, as well as insecticidal or pesticidal compositions comprising same, and methods of use thereof as pesticidal agents.

Solids exist in either amorphous or crystalline forms. In the case of crystalline forms, molecules are positioned in 3-dimensional lattice sites. When a compound recrystallizes from a solution or slurry, it may crystallize with different spatial lattice arrangements, a property referred to as "polymorphism," with the different crystal forms individually being referred to as a "polymorph". Different polymorphic forms of a given substance may differ from each other with respect to one or more physical properties, such as solubility and dissociation, true density, crystal shape, compaction behavior, flow properties, and/or solid state stability.

The inventors of the present applications, after extensive experimentation, have discovered three crystalline forms of 5-amino-1-[2,6-dichloro-4-(trifluoromethyl)phenyl]-4-[(trifluoromethyl)sulfinyl]-1H-pyrazole-3-carbonitrile (fipronil), designated Form I, Form II and Form III. The inventors have further discovered two new solvate pseudomorphs of fipronil, designated pseudomorph FS-T (a toluene hemi-solvate) and pseudomorph FS-M (an MIBK hemi-solvate). The inventors have further discovered a novel amorphous form of fipronil. These new Forms exhibit different spectral characteristics as depicted by their distinct Differential Scanning Calorimetry (DSC) thermograms, Thermal Gravimetric Analysis (TGA) spectra, X-ray diffraction patterns, and infrared (IR) spectra.

Form I

In one embodiment, the present invention provides a novel crystalline polymorphic form of 5-amino-1-[2,6-dichloro-4-(trifluoromethyl)phenyl]-4-[(trifluoromethyl)sulfinyl]-1H-pyrazole-3-carbonitrile (fipronil), designated "Form I". This novel and surprising polymorph may be characterized by, for example, by DSC, X-Ray powder diffraction spectrometry and/or IR spectrometry.

Figure 1:
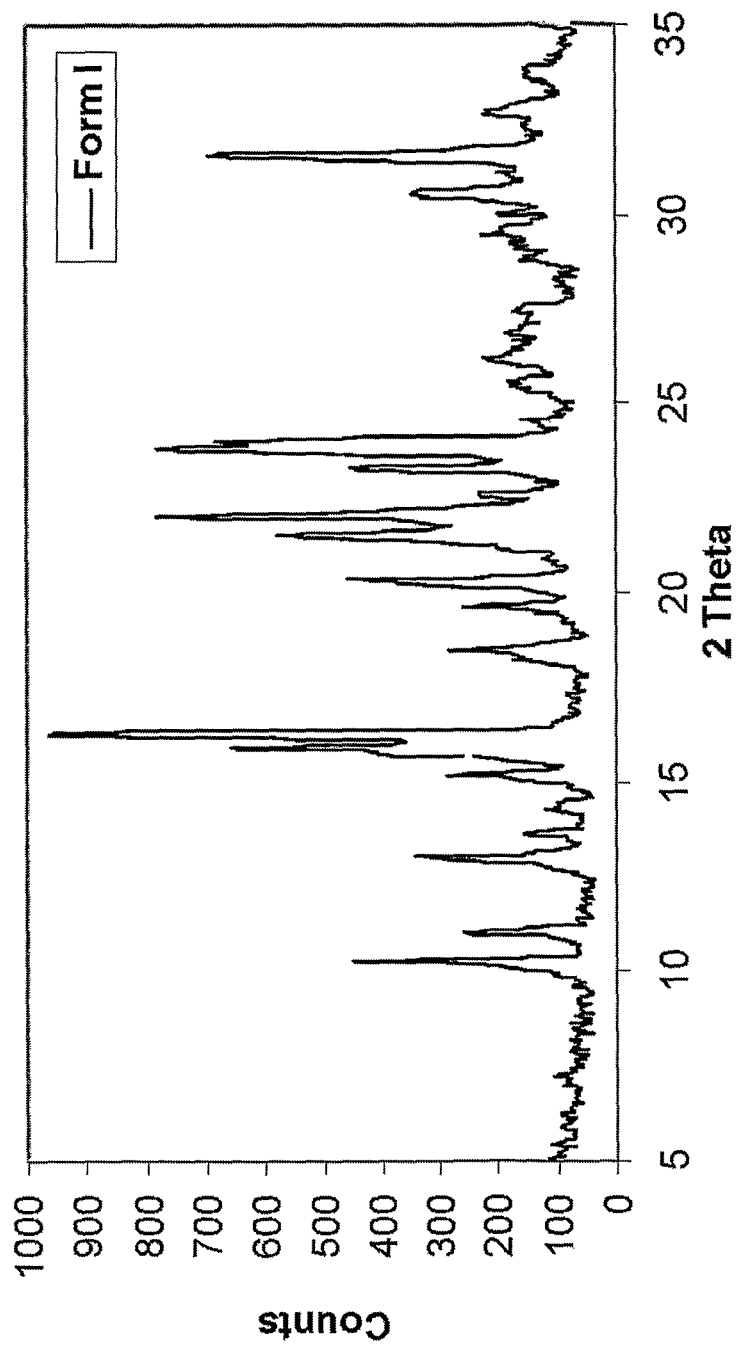
FIG. 1 is an X-ray powder diffraction spectrum of fipronil Form I.

For example, as shown in FIG. 1, Form I exhibits an X-ray powder diffraction pattern having characteristic peaks (expressed in degrees 2θ (+/−0.2°θ) at one or more of the following positions: 10.3, 11.05, 13.04, 15.93, 16.27, 18.48, 19.65, 20.34, 22.05, and 31.55. The X-Ray powder diffraction were collected on Philips powder diffractometer PW 1050/70 operated at 40 kV and 30 mA using CuKα radiation (wavelength equal to 1.54178 Å) and diffracted beam graphite monochromator. The typical 0-2θ scan range is 3-35° 2 Theta with a step size of 0.05° and a count time of 0.5 seconds per step.

The samples were grinded using agate mortar and pestle. The obtained powder is then pressed into aluminum sample holder with rectangular cavity of 20 mm*15 mm and of 0.5 mm depth.

Figure 2:
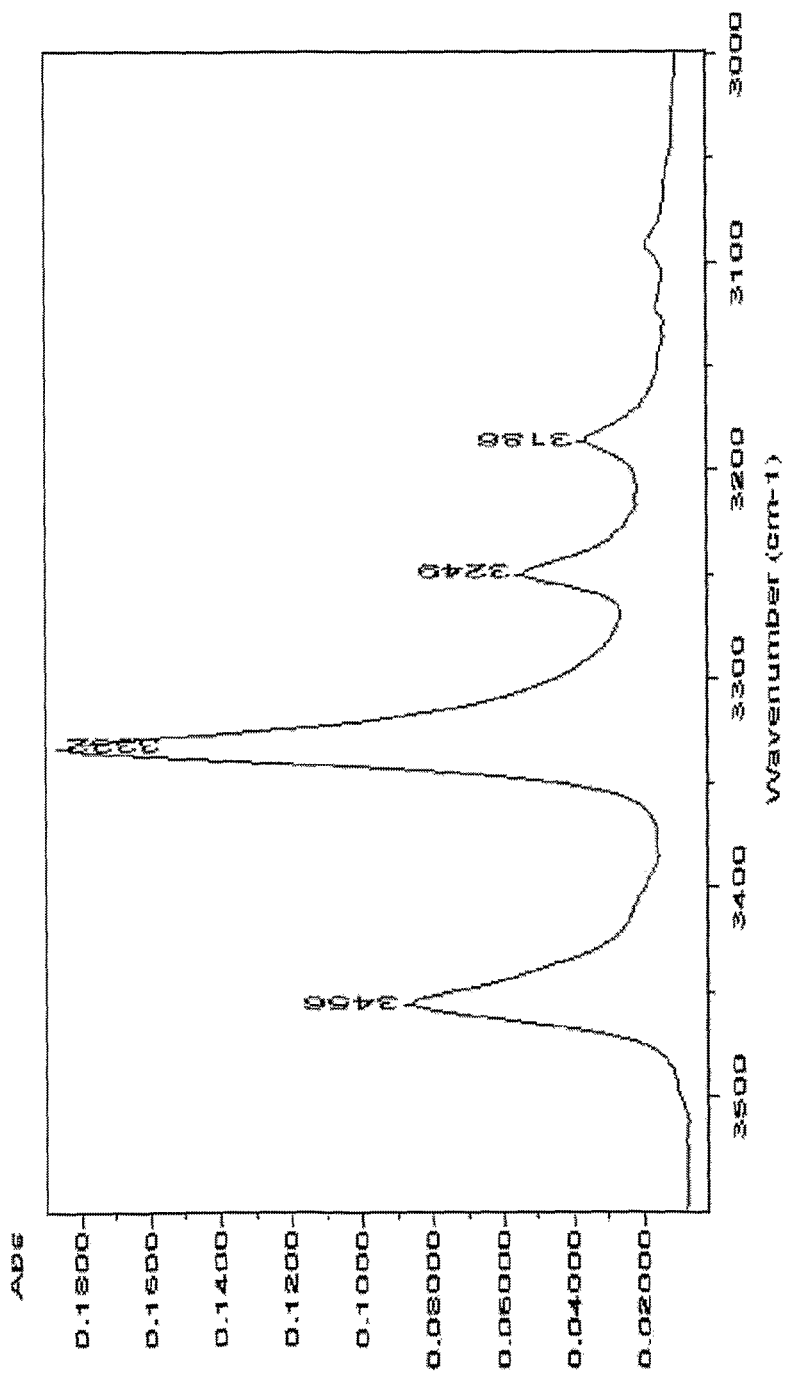
FIG. 2: is a FT Infrared spectrum of fipronil Form I (at the 3,000 cm$^{-1}$ range).

Furthermore, as shown in FIG. 2 (showing the 3000 cm$^{-1}$ range only), Form I also exhibits an Infrared (IR) spectrum having characteristic peaks at about 3332 and 3456 cm$^{-1}$, as measured by a Fourier transform infrared (FT-IR) spectrophotometer ReactIR™ 1000 of Mettler Toledo Autochem (ATR method, MCT detector), diamond window, in DuraSamplIR™ sampling device. The diamond sensor has a standard focusing optic of ZnSe. The powdered samples were compressed in the sampling device and were measured with resolution of 4 cm$^{-1}$ and 256 scans.

Figure 3:
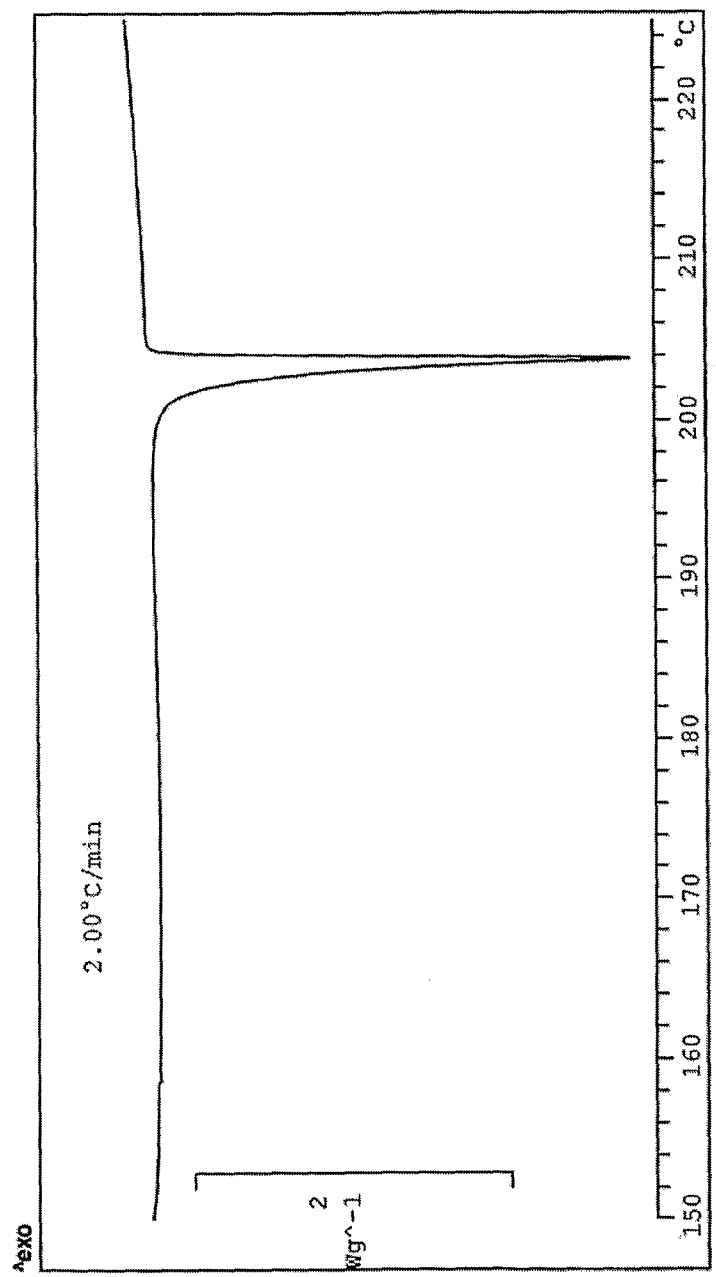
FIG. 3: is a Differential Scanning Calorimetry (DSC) thermogram of fipronil Form I.

Furthermore, as shown in FIG. 3, Form I also exhibits a Differential Scanning Calorimetry (DSC) thermogram which is characterized by a predominant endotherm peak at about 202.5° C. by DSC of Mettler Toledo with 821$^e$ module. The weighted samples (2-4 mg) were purged with nitrogen flow during the measurements at a scan rate of 2° C. and/or 10° C. per minute. Aluminum standard pierced crucibles of 40 μL were used. The evaluation is performed using STAR$^e$ software. As used herein, the term "about 202.5° C." means a range of 201° C. to 204° C. In this regard, it should be understood that the endotherm measured by a particular differential scanning calorimeter is dependent upon a number of factors, including the rate of heating (i.e., scan rate), the calibration standard utilized, instrument calibration, relative humidity, and upon the chemical purity of the sample being tested. Thus, an endotherm as measured by DSC on the instrument identified above may vary by as much as ±1.5° C.

In another aspect, the present invention provides processes for preparing the novel fipronil polymorph Form I. In one embodiment, Form I can be prepared by heating a fipronil pseudomorph FS-T to a temperature greater than about 100° C., preferably a temperature of about 150° C.; cooling, and isolating the product. Generally, although not by limitation, heating to about 150° C. for about 40 minutes is sufficient to produce fipronil Form I.

Form II

In another embodiment, the present invention provides a novel crystalline polymorphic form of 5-amino-1-[2,6-dichloro-4-(trifluoromethyl)phenyl]-4-[(trifluoromethyl) sulfinyl]-1H-pyrazole-3-carbonitrile (fipronil), designated "Form II". This novel and surprising polymorph may be characterized by, for example, by DSC, X-Ray powder diffraction spectrometry and/or IR spectrometry.

Figure 4:
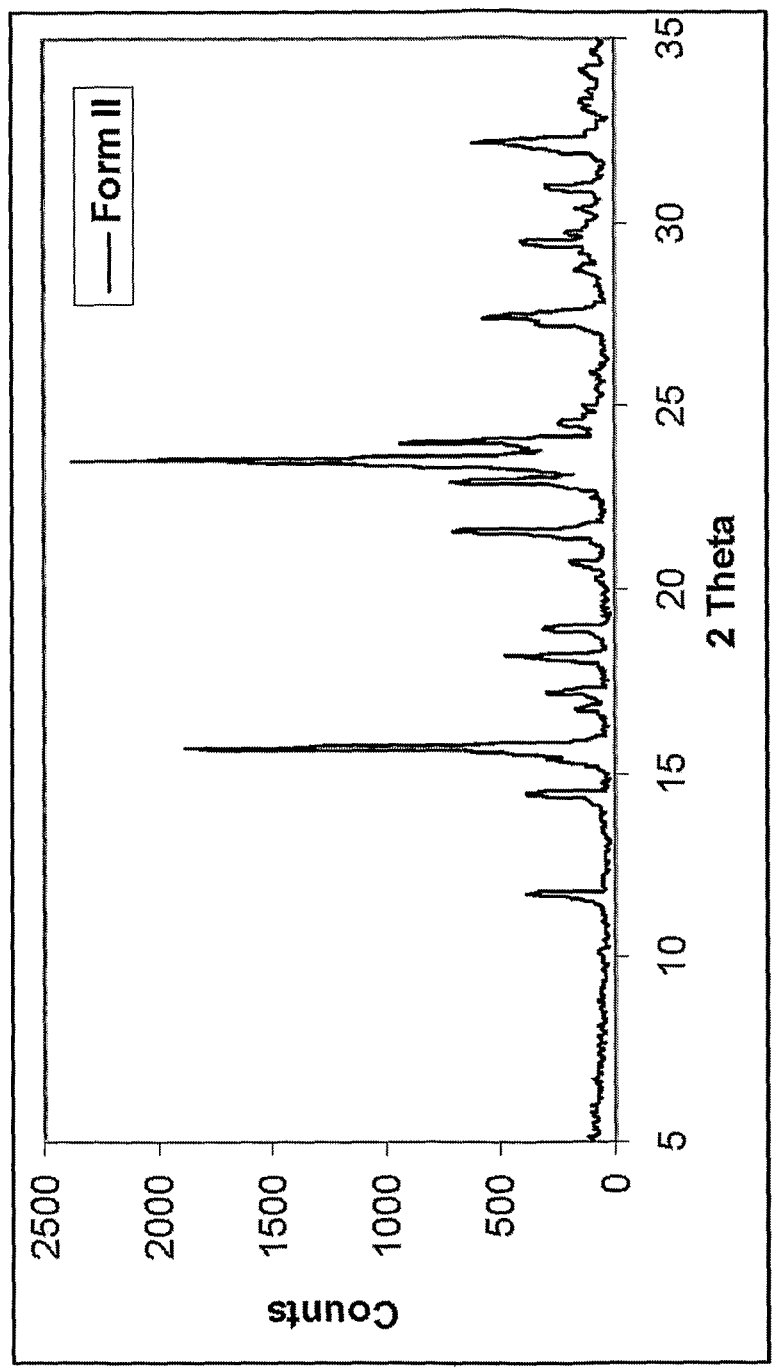
FIG. 4 is an X-ray powder diffraction spectrum of fipronil Form II.

For example, as shown in FIG. 4, Form II exhibits an X-ray powder diffraction pattern having characteristic peaks (expressed in degrees 2θ (+/−0.2°θ) at one or more of the following positions: 11.7, 14.4, 15.7, 16.75, 17.2, 18.2, 19, 20.7, 22.95, 23.55, and 24.0. The X-Ray powder diffraction was measured as described above.

Figure 5:
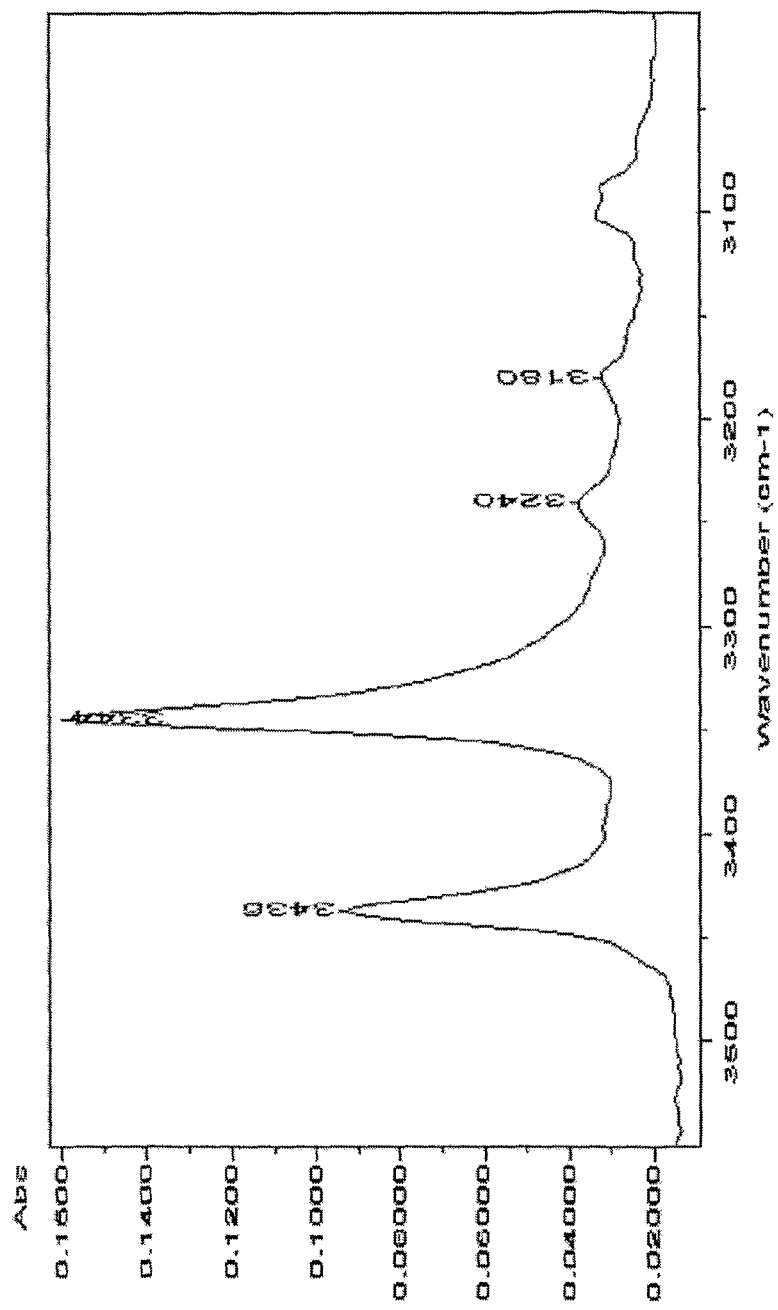
FIG. 5: is a FT Infrared spectrum of fipronil Form II (at the 3,000 cm$^{-1}$ range).

Furthermore, as shown in FIG. 5 (showing the 3000 cm$^{-1}$ range only), Form II also exhibits an Infrared (IR) spectrum having characteristic peaks at about 3344 and 3436.5 cm$^{-1}$, as measured by a Fourier transform infrared (FT-IR) spectrophotometer as described above.

Figure 6:
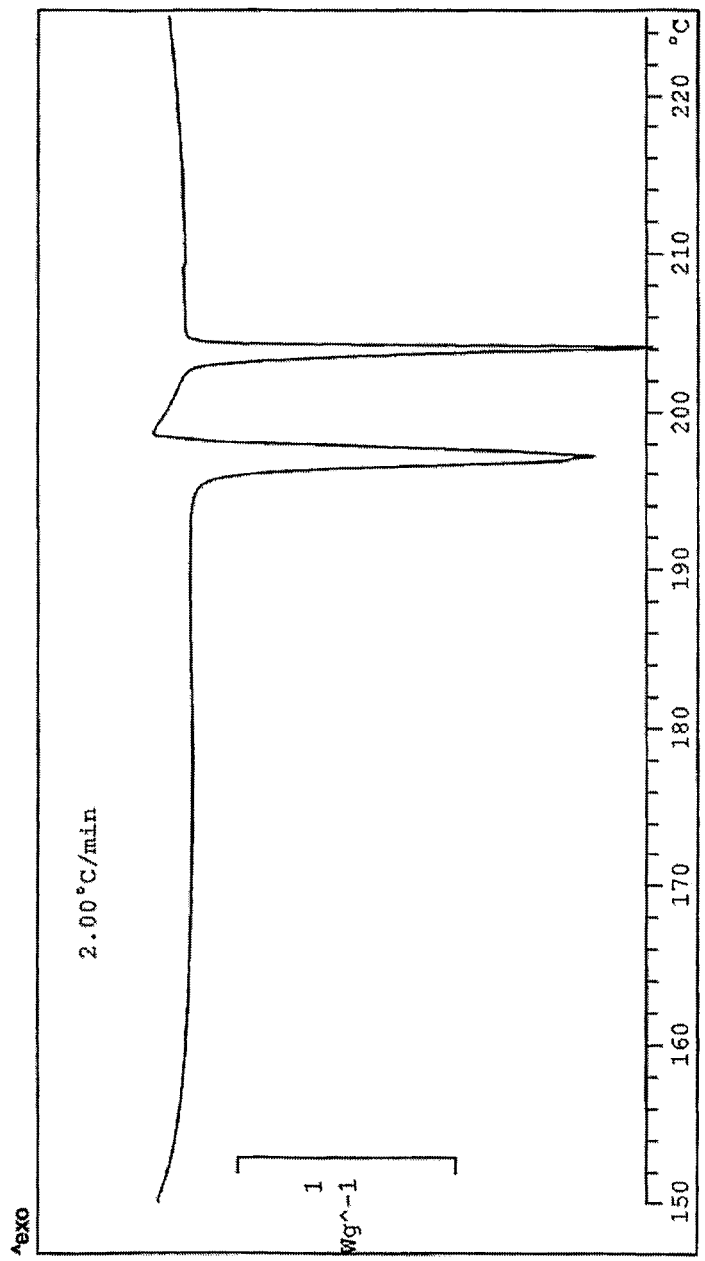
FIG. 6: is a Differential Scanning Calorimetry (DSC) thermogram of fipronil Form II.

Furthermore, as shown in FIG. 6, Form II also exhibits a DSC thermogram, which is characterized by a predominant endotherm at about 195° C. (Form II to liquid) at a scan rate of 2° C. and/or 10° C. per minute. The thermogram further shows an endotherm at about 202° C. resulting from crystallization to Form I. The thermogram was measured by a Differential Scanning Calorimeter as described above. As used herein, the term "about 195° C." means from about 193.5° C. to about 196.5° C.

In another aspect, the present invention provides processes for preparing the novel polymorph Form II. In one embodiment, Form II fipronil can be prepared by crystallizing fipronil from a solvent selected from the group consisting of isopropyl alcohol, hexane, ethyl acetate, 1-propanol, butanol, and MIBK, or any mixture of the solvents; and isolating the resulting crystals. In a currently preferred embodiment, the process includes preparing a solution of the compound in one or more of the aforementioned solvents, preferably by applying heat until dissolution is complete, cooling the solution until crystals appear. Generally, cooling the solution to room temperature (defined herein as about 20° C. to about 25° C.) is sufficient, however, the solution can be cooled to lower temperatures, for example 0° C., 5° C., 10° C., 15° C. and the like. The crystals are then isolated by any conventional method known in the art, for example by filtration, centrifugation, etc.

In one embodiment, the crystallization solvent is isopropyl alcohol. In another embodiment, the crystallization solvent is a mixture of ethyl acetate and n-hexane. In yet another embodiment, the crystallization solvent is a mixture of n-hexane and MIBK. When a solvent mixture is used, fipronil can be dissolved in one solvent followed by the addition of the other, or fipronil can be simultaneously dissolved in the solvent mixture.

Also, the reaction can be seeded with Form II seeds in order to induce crystallization, as known in the art.

The fipronil starting material used for preparing Form II can be any form of fipronil, including the fipronil described in U.S. Pat. No. 5,232,940, amorphous fipronil, fipronil Form I, fipronil Form III, fipronil FS-T, fipronil FS-M, or any other fipronil known in the art.

Form III

In one embodiment, the present invention provides a novel crystalline polymorphic form of 5-amino-1-[2,6-dichloro-4-(trifluoromethyl)phenyl]-4-[(trifluoromethyl)sulfinyl]-1H-pyrazole-3-carbonitrile (fipronil), designated "Form III". This novel and surprising polymorph may be characterized by, for example, by X-Ray powder diffraction spectrometry.

Figure 7:
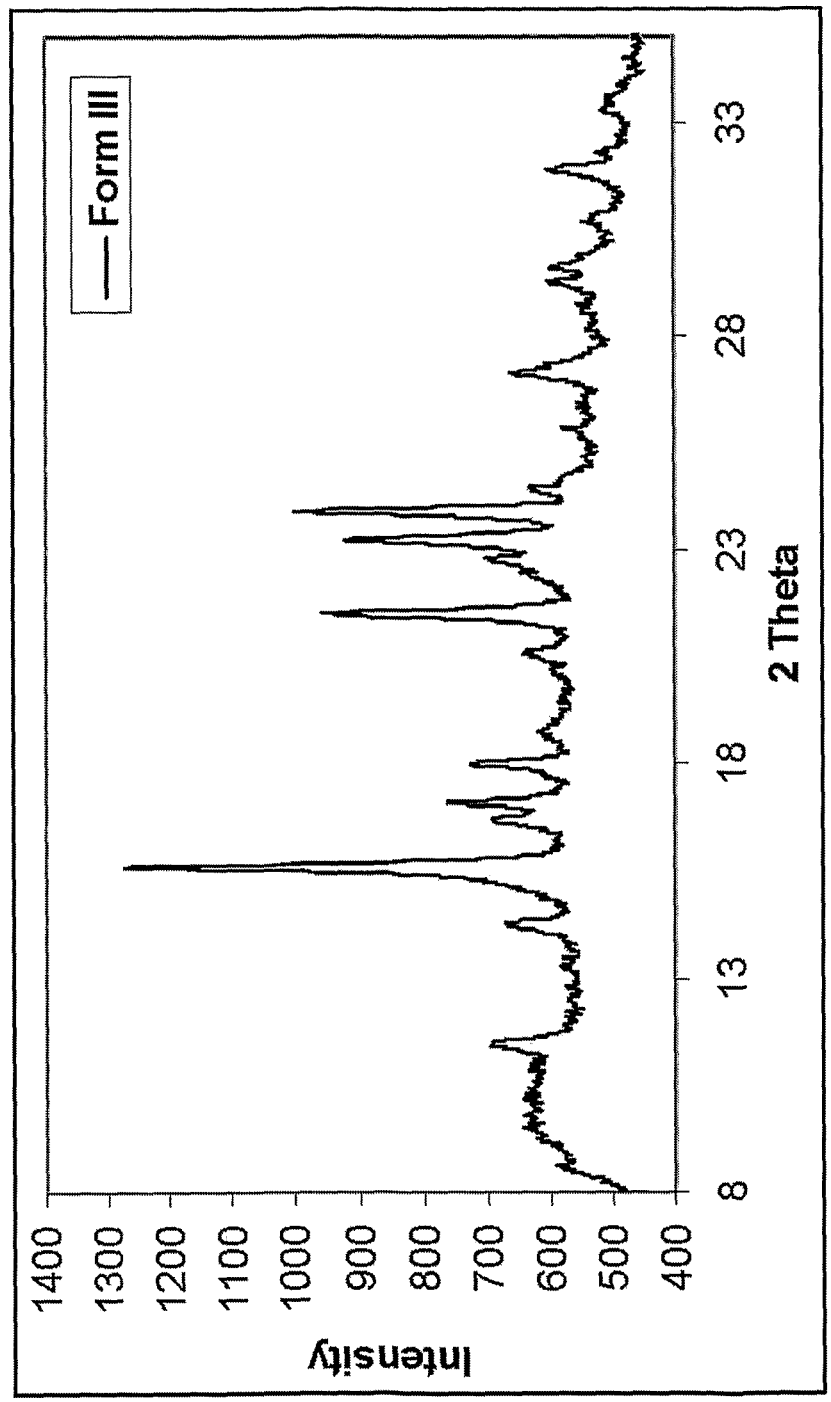
FIG. 7: is an X-ray powder diffraction spectrum of a fipronil Form III.

For example, as shown in FIG. 7, Form III exhibits an X-ray powder diffraction pattern having characteristic peaks (expressed in degrees 2θ (+/−0.2°θ) at one or more of the following positions: 15.6, 16.7, 17.1, 27.2, and 31.9. The X-Ray powder diffraction was measured as described above.

The DSC of form FS-T at scan rate of 10° C. per minute (FIG. 8) shows an endothermic transformation of FS-T to Form III at ~110° C. and the exothermic transformation of form III to form I at 150° C.

In another aspect, the present invention provides processes for preparing the novel fipronil polymorph Form III. In one embodiment, Form III is an intermediate in the conversion of pseudomorph FS-T to Form I. As a result of heating FS-T, solvent liberation occurs resulting in the formation of Form III, which then undergoes exothermic transition to Form I.

Form FS-T

In another embodiment, the present invention provides a novel toluene hemi solvate pseudomorph of 5-amino-1-[2,6-dichloro-4-(trifluoromethyl)phenyl]-4-[(trifluoromethyl) sulfinyl]-1H-pyrazole-3-carbonitrile (fipronil), designated "FS-T". This novel and surprising pseudomorph may be characterized by, for example, by TGA, X-Ray powder diffraction spectrometry and/or IR spectrometry.

Figure 10:
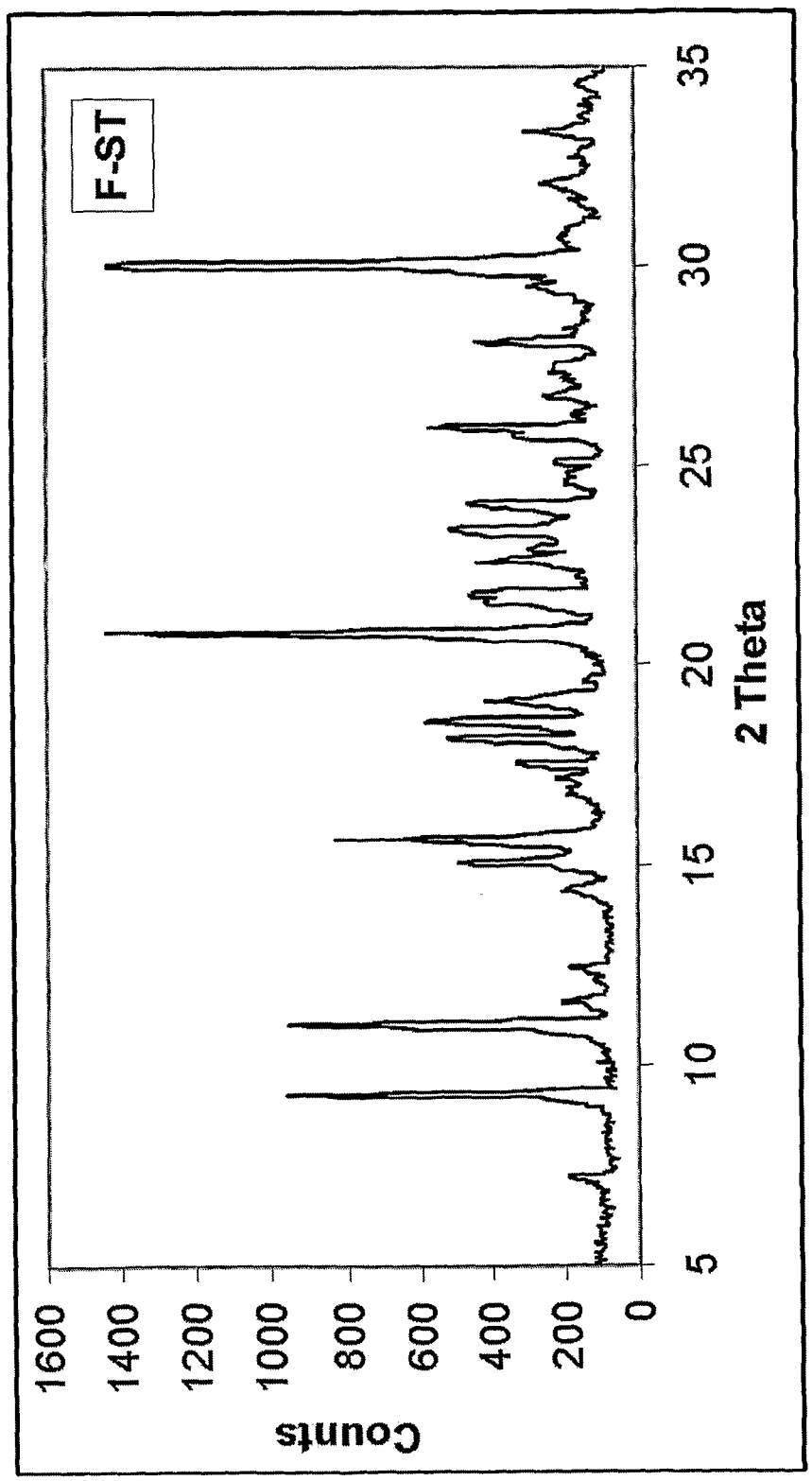
FIG. 10: is an X-ray powder diffraction spectrum of a fipronil pseudomorph toluene hemi-solvate (F-ST).

For example, as shown in FIG. 10, pseudomorph FS-T exhibits an X-ray powder diffraction pattern having characteristic peaks (expressed in degrees 2θ (+/−0.20°θ) at one or more of the following positions: 7.2, 9.3, 12.5, 15.1, 18.65, 19.15, 20.85, 25.95, 28.1, 30.05, and 33.40. The X-Ray powder diffraction was measured as described above.

Figure 11:
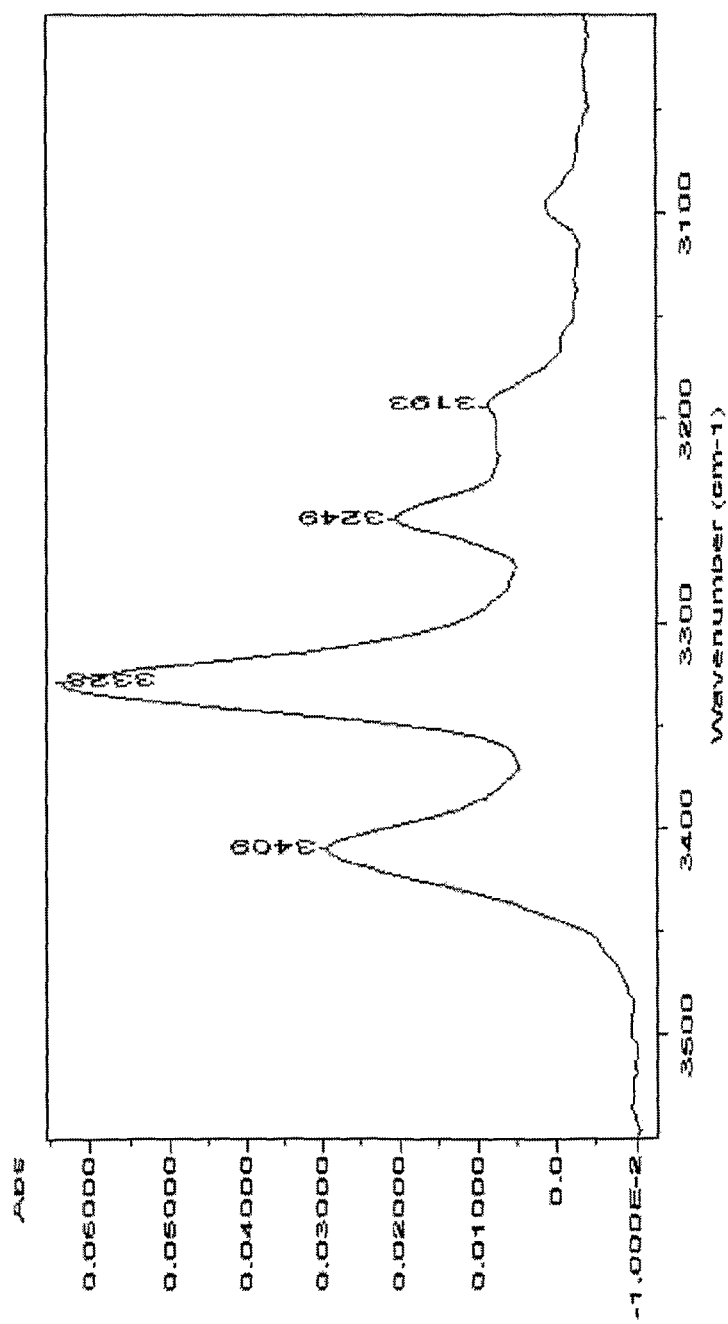
FIG. 11: is a FT Infrared spectrum of fipronil F-ST (at the 3,000 cm$^{-1}$ range).

Furthermore, as shown in FIG. 11 (showing the 3000 cm$^{-1}$ range only), pseudomorph FS-T also exhibits an IR spectrum having characteristic peaks at about 694.6 and 733.2 cm$^{-1}$ (toluene solvent); and 3328.4 and 3409.5 cm$^{-1}$ (NH$_2$ asymmetric and symmetric stretches), as measured by a Fourier transform infrared (FT-IR) spectrophotometer as described above.

Figure 9:
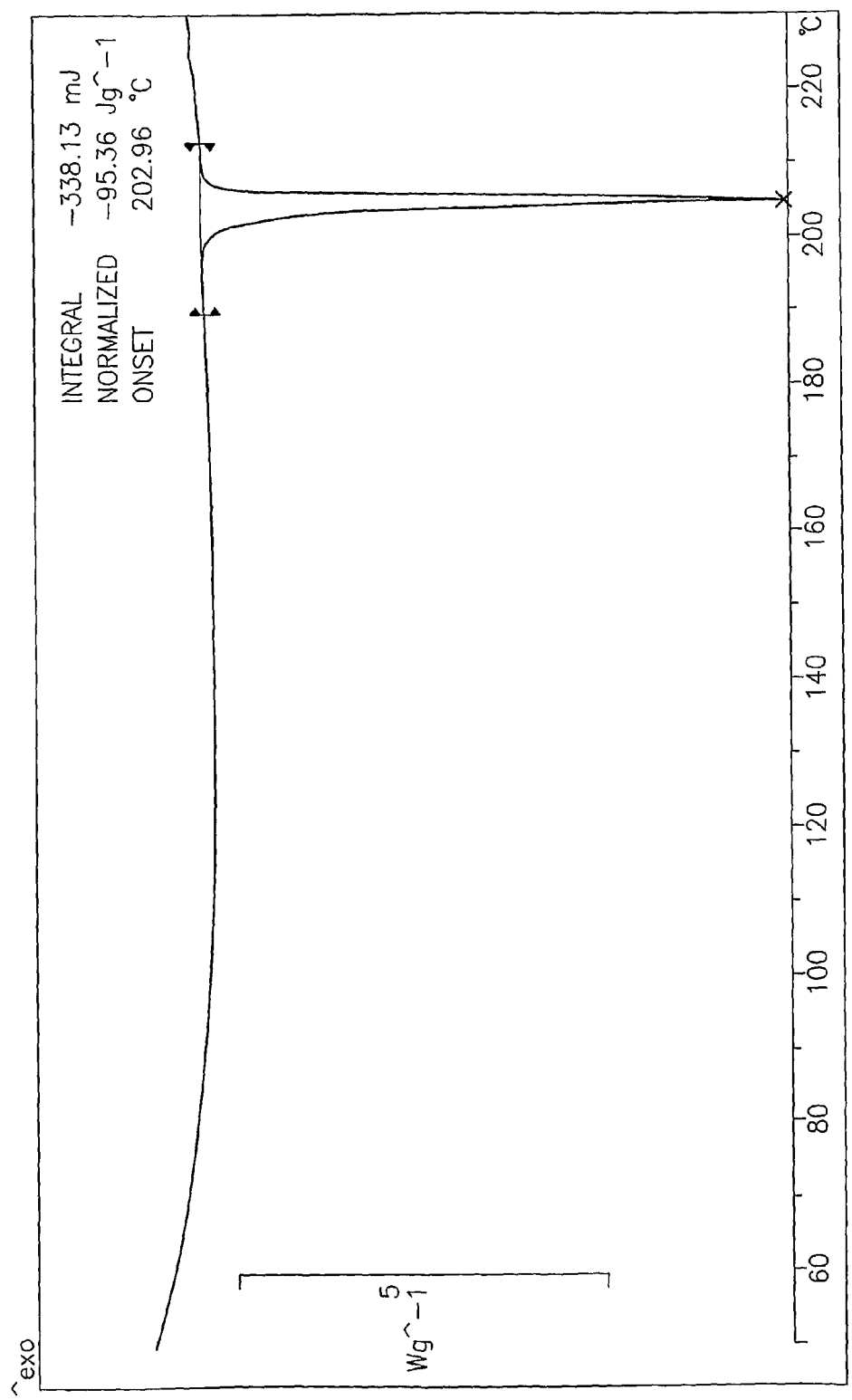
FIG. 9: is a Differential Scanning Calorimetry (DSC) thermogram of fipronil pseudomorph toluene hemi-solvate (FS-T) after heating in steps to 150° C. and cooling to 60° C.

Upon stepwise heating to 150° C. and cooling to 60° C., fipronil FS-T converts to Form I, as shown in FIG. 9.

In another aspect, the present invention provides processes for preparing the novel pseudomorph FS-T. In one embodiment, fipronil FS-T can be prepared by crystallizing fipronil from toluene. In a currently preferred embodiment, the process includes preparing a solution of the compound is toluene, preferably by applying heat until dissolution is complete, cooling the solution until crystals appear, and isolating the crystals. Generally, cooling the solution to room temperature (defined herein as about 20° C. to about 25° C.) is sufficient, however, the solution can be cooled to lower temperatures, for example 0° C., 5° C., 10° C., 15° C. and the like. The crystals are then isolated by any conventional method known in the art, for example by filtration, centrifugation, etc.

Also, the reaction can be seeded with pseudomorph FS-T seeds in order to induce crystallization, as known in the art.

The fipronil starting material used for preparing pseudomorph FS-T can be any form of fipronil, including the fipronil described in U.S. Pat. No. 5,232,940, amorphous fipronil, fipronil Form I, fipronil Form II, fipronil Form III, fipronil FS-M, or any other fipronil known in the art.

Form FS-M

In another embodiment, the present invention provides a novel methyl isobutyl ketone (MIBK) hemi solvate pseudomorph of 5-amino-1-[2,6-dichloro-4-(trifluoromethyl)phenyl]-4-[(trifluoromethyl)sulfinyl]-1H-pyrazole-3-carbonitrile (fipronil), designated "FS-M". This novel and surprising pseudomorph may be characterized by, for example, by TGA, X-Ray powder diffraction spectrometry and/or IR spectrometry.

Figure 12:
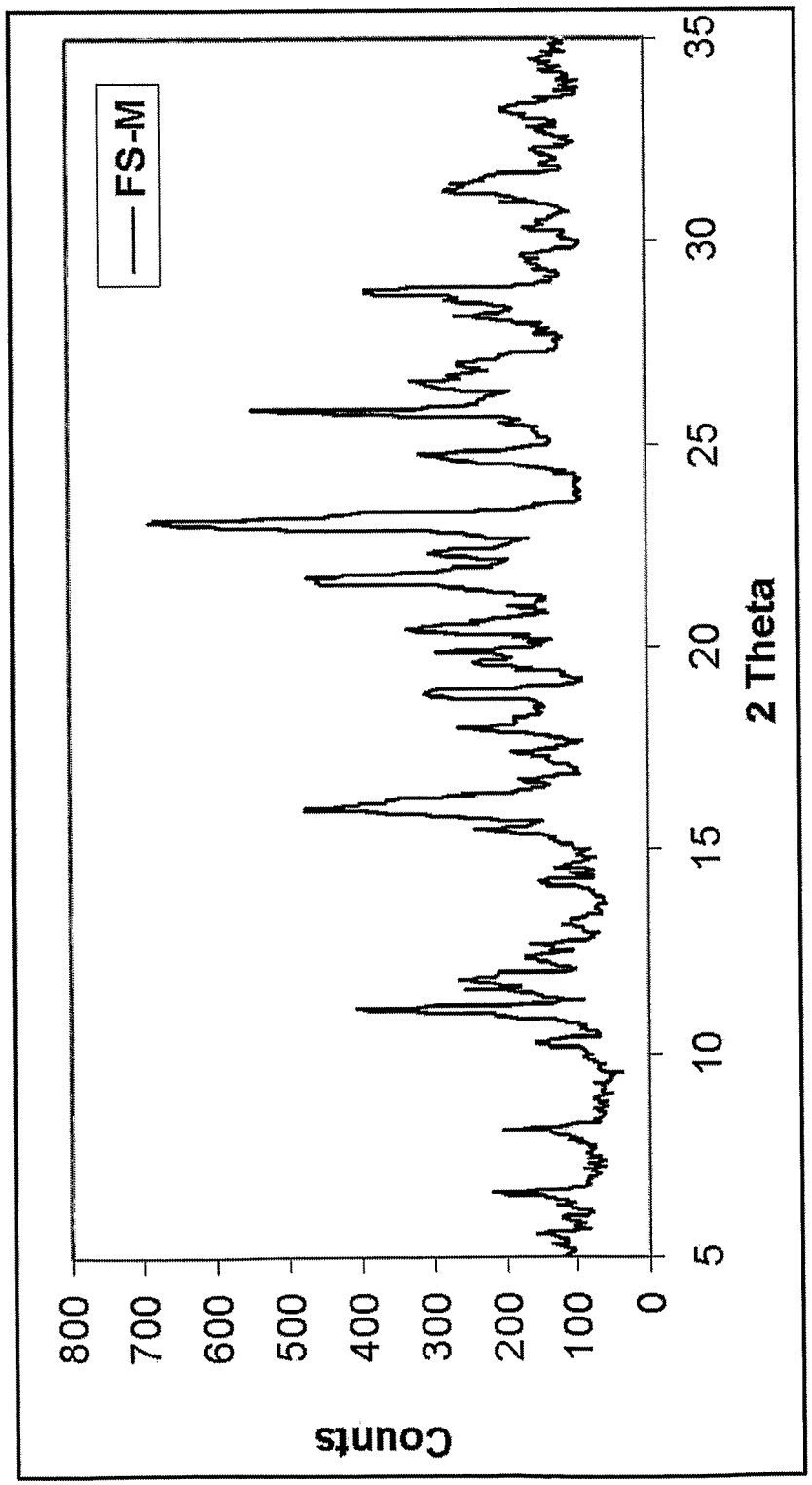
FIG. 12: is an X-ray powder diffraction spectrum of a fipronil pseudomorph MIBK hemi-solvate (F-SM).

For example, as shown in FIG. 12, pseudomorph FS-M exhibits an X-ray powder diffraction pattern having characteristic peaks (expressed in degrees 2θ (+/−0.2°θ) at one or more of the following positions: 6.6, 8.15, 11.85, 19.95, 20.45, 23.10, 26.6, 28.8, and 31.30. The X-Ray powder diffraction was measured as described above.

Figure 8:
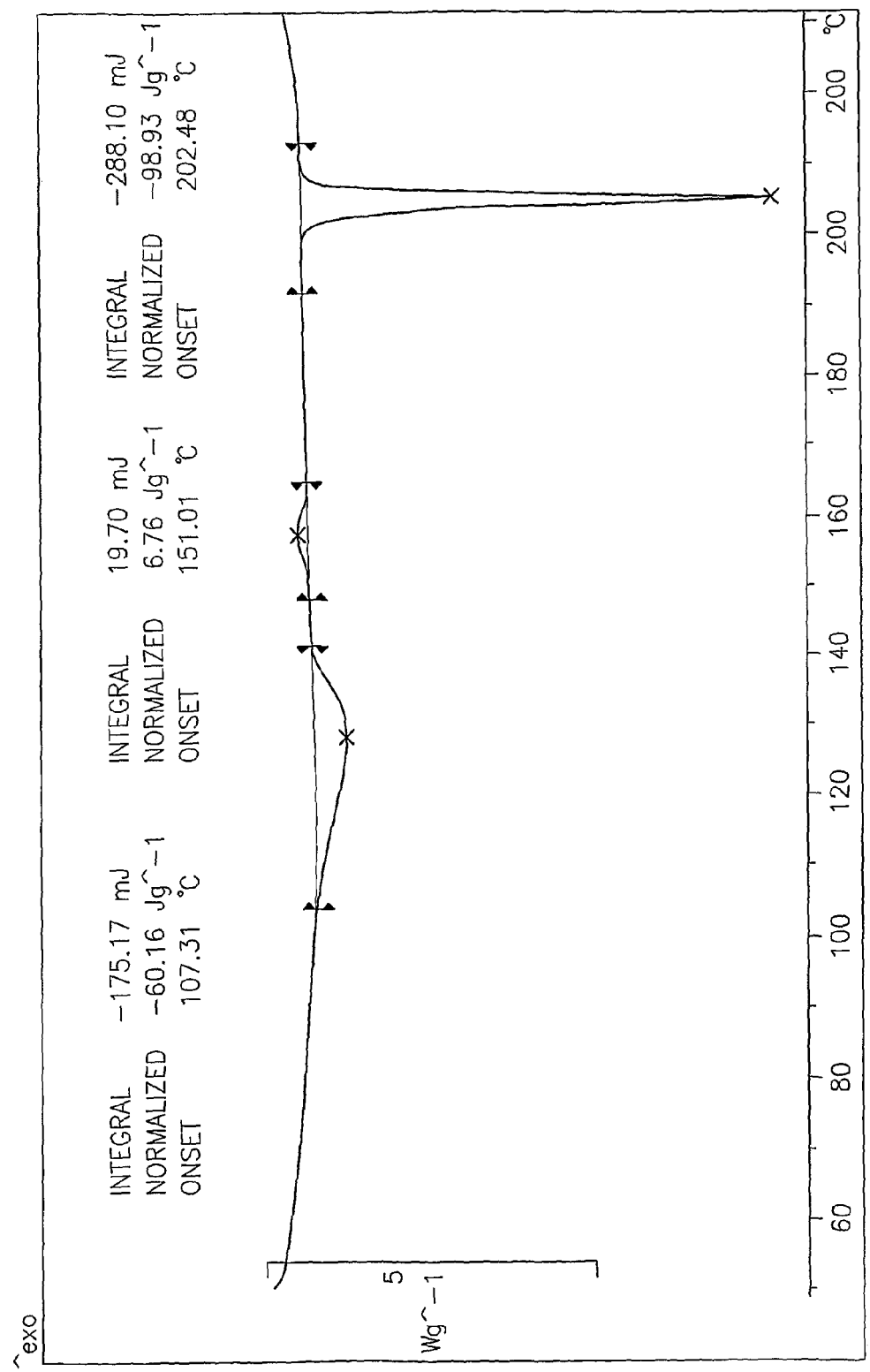
FIG. 8: is a Differential Scanning Calorimetry (DSC) thermogram of fipronil pseudomorph toluene hemi-solvate (FS-T) and the phase transition to Form III and to Form I.
Figure 13:
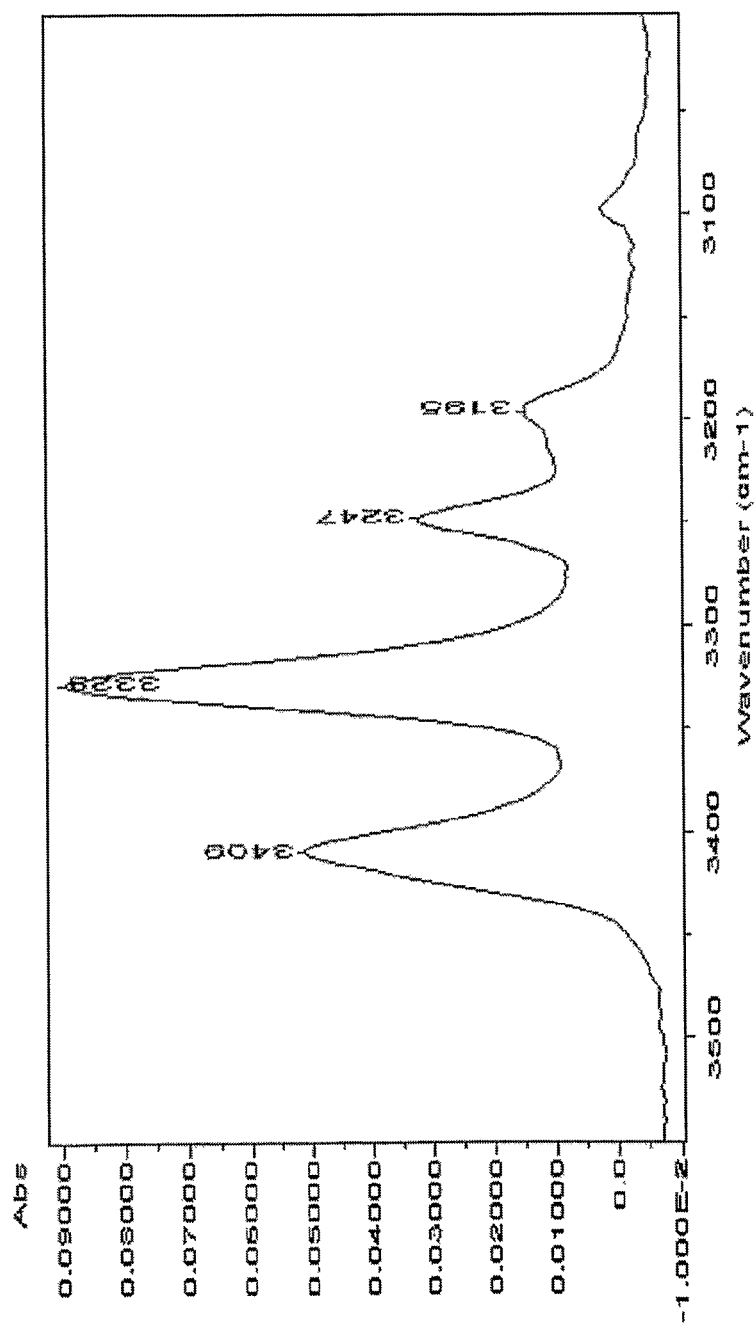
FIG. 13: is a FT Infrared spectrum of fipronil F-SM (at the 3,000 cm$^{-1}$ range).

Furthermore, as shown in FIG. 13 (showing the 3000 cm$^{-1}$ range only), pseudomorph FS-M also exhibits an IR spectrum substantially as shown in FIG. 8, having characteristic peaks at about 1710 cm$^{-1}$ (MIBK ketone); and 3409.5 and 3328 cm$^{-1}$ (NH$_2$ asymmetric and symmetric stretches), as measured by a Fourier transform infrared (FT-IR) spectrophotometer as described above.

Figure 14:
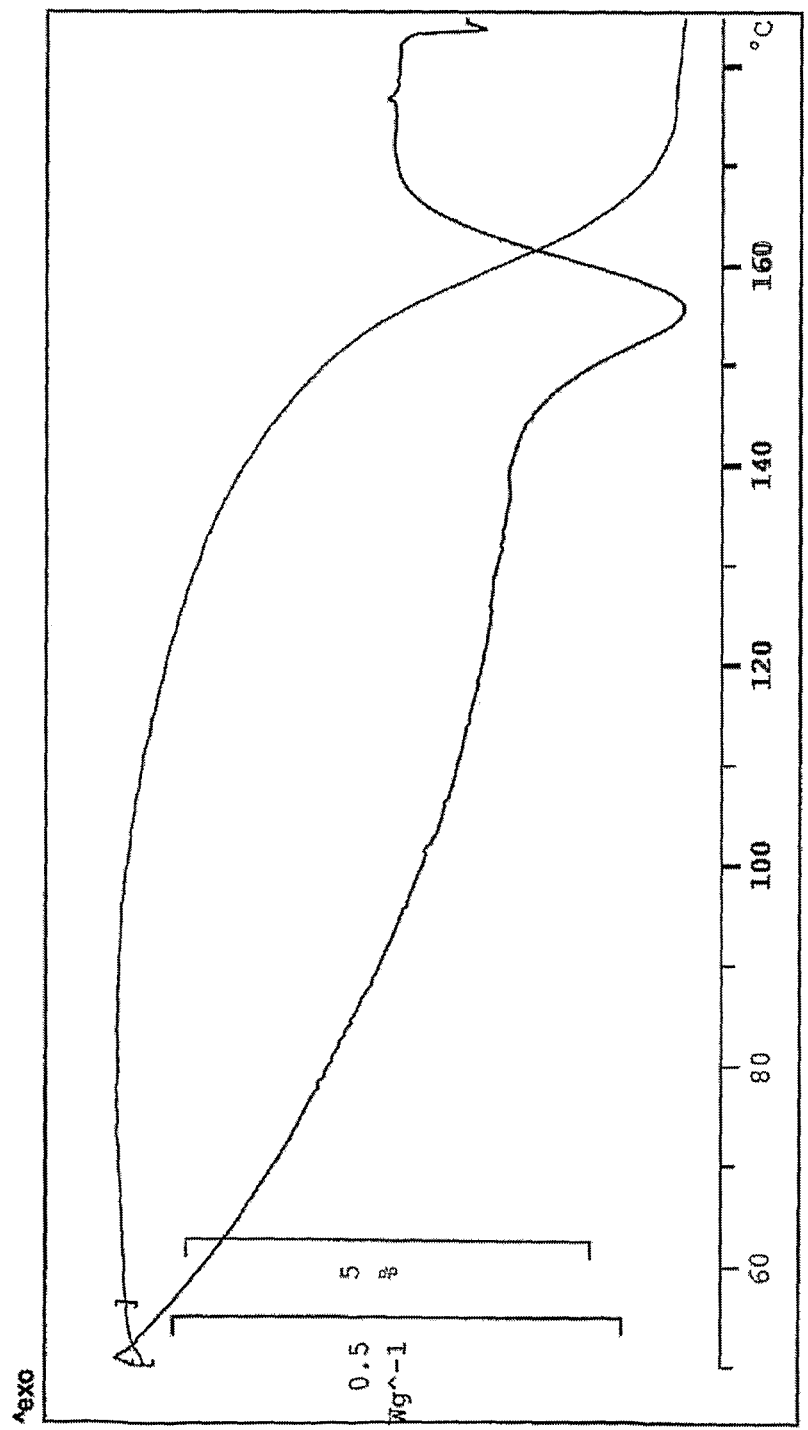
FIG. 14: is a Differential Scanning Calorimetry (DSC) thermogram embedded with TGA (Thermal Gravimetric Analysis) thermogram of fipronil F-SM.

Furthermore, pseudomorph FS-M also exhibits a DSC thermogram embedded with TGA thermogram substantially as shown in FIG. 14.

In another aspect, the present invention provides processes for preparing the novel pseudomorph FS-M. In one embodiment, pseudomorph FS-M fipronil can be prepared by crystallizing fipronil from MIBK and n-hexane. Generally, fipronil is dissolved in MIBK and n-hexane (either simultaneously or sequentially), preferably with heat, and the flask is left to stand in the air so that the solvent slowly evaporates. Gradually, crystals begin to appear, which are then isolated. Generally, only a part of the solvent evaporates before the crystals begin to appear, for example about 10-90% of the solvent evaporates in the air, leading to the appearance of crystals.

Also, the reaction can be seeded with pseudomorph FS-M seeds in order to induce crystallization, as known in the art.

The fipronil starting material used for preparing pseudomorph FS-M can be any form of fipronil, including amorphous fipronil, fipronil Form I, fipronil Form II, fipronil Form III, fipronil FS-T, or any other fipronil known in the art.

Amorphous Fipronil

In another embodiment, the present invention provides a novel amorphous fipronil. This novel and surprising amorphous form may be characterized by, for example, X-Ray powder diffraction spectrometry.

Figure 15:
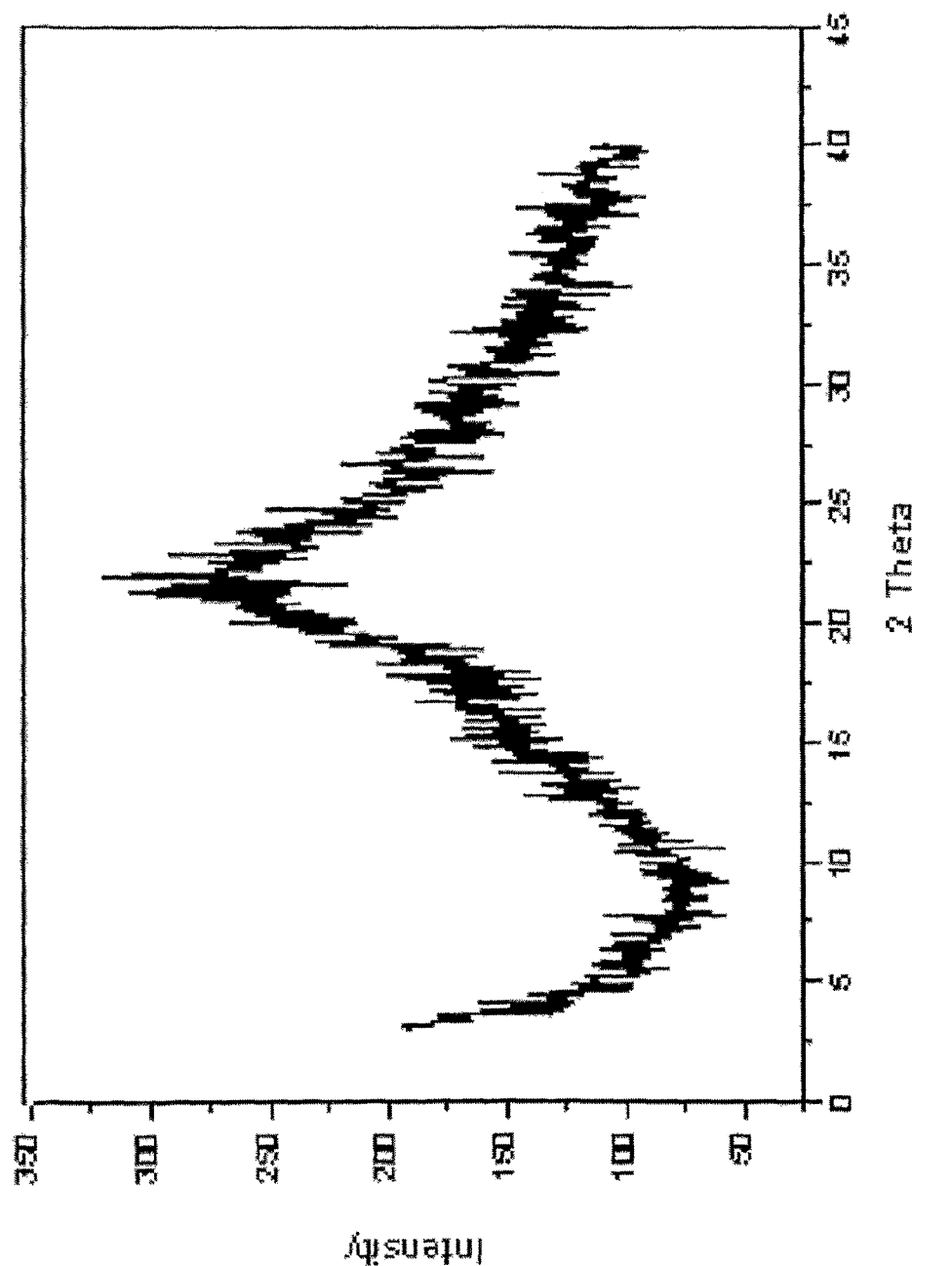
FIG. 15: is an X-ray powder diffraction spectrum of amorphous fipronil.

For example, as shown in FIG. 15, the amorphous form has an X-ray powder diffraction pattern showing no significant signals, indicating an amorphous fipronil solid.

In another aspect, the present invention provides processes for preparing the novel amorphous fipronil. In one embodiment, amorphous fipronil is prepared by heating fipronil to a temperature greater than its melting point (preferably to a temperature greater than about 202.5° C., more preferably to a temperature of about 215° C.), and cooling.

The fipronil starting material used for preparing amorphous fipronil can be any form of fipronil, including amorphous fipronil, fipronil Form I, fipronil Form II, fipronil Form III, fipronil FS-T, fipronil FS-M, or any other fipronil known in the art.

Fipronil Form I and Form II Mixtures

In another embodiment, the present invention provides a mixture of polymorphic Form I and Form II of 5-amino-1-[2, 6-dichloro-4-(trifluoromethyl)phenyl]-4-[(trifluoromethyl) sulfinyl]-1H-pyrazole-3-carbonitrile (fipronil). Preferably, the mixture comprises from about 10% to about 90% by weight of fipronil Form I, and from about 90% to about 10% by weight fipronil Form II. In another embodiment, the mixture comprises from about 20% to about 80% by weight of fipronil Form I, and from about 80% to about 20% by weight fipronil Form II. In yet another embodiment, the mixture comprises from about 30% to about 70% by weight of fipronil Form I, and from about 70% to about 30% by weight fipronil Form II. In yet another embodiment, the mixture comprises from about 40% to about 60% by weight of fipronil Form I, and from about 60% to about 40% by weight fipronil Form II. In yet another embodiment, the mixture comprises about 50% of fipronil Form I, and about 50% by weight fipronil Form II.

In one embodiment, the mixture can be prepared by mixing fipronil Form I and Form II at the appropriate and desired range.

Compositions and Uses

Fipronil is widely known to be effective in controlling pests. Thus, in another aspect, the present invention provides pesticidal compositions comprising the novel crystalline polymorphs, the novel solvate pseudomorphs and/or the novel amorphous fipronil, which are useful for controlling pests. In one embodiment, the compositions comprise a pesticidally effective amount of crystalline polymorph Form I of fipronil; and an acceptable adjuvant. In another embodiment, the composition comprises a pesticidally effective amount of crystalline polymorph Form II of fipronil; and an acceptable adjuvant. In another embodiment, the composition comprises a pesticidally effective amount of crystalline polymorph Form III of fipronil; and an acceptable adjuvant. In yet another embodiment, the composition comprises a pesticidally effective amount of pseudomorph FS-T of fipronil; and an acceptable adjuvant. In yet another embodiment, the composition comprises a pesticidally effective amount of pseudomorph FS-M of fipronil; and an acceptable adjuvant. In yet another embodiment, the composition comprises a pesticidally effective amount of an amorphous fipronil; and an acceptable adjuvant.

The compositions of the invention can be applied to control pests in compositions of any type known to the art suitable for internal or external administration to vertebrates or application for the control of arthropods in any premises or indoor or outdoor area. All such compositions may be prepared in any manner known to the art.

The present invention also provides methods of controlling pests at a locus, by administering the compositions of the present invention.

Examples of the pests that may be controlled are generally described in European Patent Application EP-A-0 295 117 and U.S. Pat. No. 5,232,940, which are incorporated by reference herein in their entirety. Illustrative of specific parasites of various host animals which may be controlled by the present invention include but are note limited to arthropods such as mites (e.g., mesostigmatids, itch, mange, scabies, chiggers), ticks (e.g., soft-bodied and hard-bodied), lice (e.g., sucking, biting), fleas (e.g., dog flea, cat flea, oriental rat flea, human flea), true bugs (e.g., bed bugs, Triatomid bugs), bloodsucking adult flies (e.g., horn fly, horse fly, stable fly, black fly, deer fly, louse fly, tsetse fly, mosquitoes), and parasitic fly maggots (e.g., bot fly, blow fly, screwworm, cattle grub, fleeceworm); helminths such as nematodes (e.g., threadworm, lungworm, hookworm, whipworm, nodular worm, stomach worm, round worm, pinworm, heartworm), cestodes (e.g., tapeworms) and trematodes (e.g., liver fluke, blood fluke); protozoa such as coccidia, trypanosomes, trichomonads, amoebas and plasmodia; acanthocephalans such as thorny-headed worms (e.g., lingulatulida); and pentastomids such as tongue worms. Arthropod pests that are particularly well controlled by the present invention are fleas and ticks.

It will be understood that by the term "animals" is meant mammals, preferably domestic animals, e.g., pets, or commercial animals, that is, animals intended to produce a commercial product such as leather or wool, e.g., cows, sheep and horses; and mammals in captivity such as zebras, lions or bears. It will be understood that by the term "pets" is meant, for example, dogs or cats.

The composition of the invention may further comprise a carrier for use in veterinary medicine, animal health, agriculture, or public health. Such compositions as generally described in EP-A-0 295 117, U.S. Pat. No. 5,232,940, and in U.S. Pat. No. 6,346,542, all of which are incorporated by reference herein in their entirety.

Compositions can be formulated, e.g., for oral, transdermal, percutaneous, e.g. pour-on, or topical administration.

Compositions for oral administration comprise the active ingredient together with pharmaceutically acceptable carriers or coatings and include, for example, tablets, pills, capsules, pastes, gels, drenches, medicated feeds, medicated drinking water, medicated dietary supplements, slow-release boluses or other slow-release devices intended to be retained within the gastro-intestinal tract. Any of these may incorporate active ingredient contained within microcapsules or coated with acid-labile or alkali-labile or other pharmaceutically acceptable enteric coatings. Feed premixes and concentrates containing the novel fipronil Forms for use in preparation of medicated diets, drinking water or other materials for consumption by animals can also be used.

Compositions for parenteral administration include solutions, emulsions or suspensions in any suitable pharmaceutically acceptable vehicle and solid or semisolid subcutaneous implants or pellets designed to release active ingredient over a protracted period and may be prepared and made sterile in any appropriate manner known to the art.

Compositions for percutaneous and topical administration include sprays, dusts, baths, dips, showers, jets, greases, shampoos, creams, wax-smears, or pour-on preparations and devices (e.g. ear tags) attached externally to animals in such a way as to provide local or systemic arthropod control.

Solid or liquid baits suitable for controlling arthropods comprise one or more of the novel Fipronil Forms of the invention and a carrier or diluent which may include a food substance or some other substance to induce consumption by the arthropod.

Liquid compositions include water miscible concentrates, emulsifiable concentrates, flowable suspensions, wettable or soluble powders containing one or more of the compounds of the invention which may be used to treat substrates or sites infested or liable to infestation by arthropods including premises, outdoor or indoor storage or processing areas, containers or equipment and standing or running water.

Solid homogenous or heterogenous compositions containing one or more of the novel fipronil Forms, for example granules, pellets, briquettes or capsules, may be used to treat standing or running water over a period of time. A similar effect may be achieved using trickle or intermittent feeds of water dispersible concentrates.

Compositions in the form of aerosols and aqueous or non-aqueous solutions or dispersions suitable for spraying, fogging and low- or ultra-low volume spraying can also be used.

Suitable solid diluents which may be used in the preparation of the compositions of the invention include aluminium silicate, kieselguhr, corn husks, tricalcium phosphate, powdered cork, absorbent carbon black, magnesium silicate, a clay such as kaolin, bentonite or attapulgite, and water soluble polymers and such solid compositions may, if desired, contain one or more compatible wetting, dispersing, emulsifying or colouring agents which, when solid, may also serve as diluent.

Such solid compositions, which may take the form of dusts, granules or wettable powders, are generally prepared by impregnating the solid diluents with solutions of the active ingredient in volatile solvents, evaporating the solvents and, if necessary, grinding the products so as to obtain powders and, if desired, granulating or compacting the products so as to obtain granules, pellets or briquettes or by encapsulating finely divided active ingredient in natural or synthetic polymers, e.g. gelatin, synthetic resins and polyamides.

The wetting, dispersing and emulsifying agents which may be present, particularly in wettable powders, may be of the ionic or non-ionic types, for example sulphoricinoleates, quaternary ammonium derivatives or products based upon condensates of ethylene oxide with nonyl- and octylphenol, or carboxylic acid esters of anhydrosorbitols which have been rendered soluble by etherification of the free hydroxy groups by condensation with ethylene oxide, or mixtures of these types of agents. Wettable powders can be treated with water immediately before use to give suspensions ready for application.

Liquid compositions for use in the present invention may take the form of solutions, suspensions and emulsions of the fipronil active ingredient optionally encapsulated in natural or synthetic polymers, and may, if desired, incorporate wetting, dispersing or emulsifying agents. These emulsions, suspensions and solutions may be prepared using aqueous, organic or aqueous-organic diluents, for example acetophenone, isophorone, toluene, xylene, mineral, animal or vegetable oils, and water soluble polymers (and mixtures of these diluents), which may contain wetting, dispersing or emulsifying agents of the ionic or non-ionic types or mixtures thereof, for example those of the types described above. When desired, the emulsions containing the fipronil active ingredient may be used in the form of self-emulsifying concentrates containing the active substance dissolved in the emulsifying agents or in solvents containing emulsifying agents compatible with the active substance, the simple addition of water to such concentrates producing compositions ready for use.

Compositions which can be applied to control arthropod, plant nematode, helminth or protozoan pests, can also contain synergists (e.g. piperonyl butoxide or sesamex), stabilizing substances, other insecticides, acaricides, plant nematocides, anthelmintics or anticoccidials, fungicides (agricultural or veterinary as appropriate e.g. benomyl, iprodione), bactericides, arthropod or vertebrate attractants or repellents or pheromones, reodorants, flavouring agents, dyes and auxiliary therapeutic agents, e.g. trace elements. These can be designed to improve potency, persistence, safety, uptake where desired, spectrum of pests controlled or to enable the composition to perform other useful functions in the same animal or area treated.

Examples of other pesticidally-active compounds which can be included in, or used in conjunction with, the compositions of the present invention are: acephate, chlorpyrifos, demeton-5-methyl, disulfoton, ethoprofos, fenitrothion, malathion, monocrotophos, parathion, phosalone, pirimiphos-methyl, triazophos, cyfluthrin, cypermethrin, deltamethrin, fenpropathrin, fenvalerate, permethrin, aldicarb, carbosulfan, methomyl, oxamyl, pirimicarb, bendiocarb, teflubenzuron, dicofol, endosulfan, lindane, benzoximate, cartap, cyhexatin, tetradifon, avermectins, ivermectin, milbemycins, thiophanate, trichlorfon, dichlorvos, diaveridine and dimetridazole.

The compositions for application to control pests usually contain from 0.00001% to 95%, more particularly from 0.0005% to 50%, by weight of the active ingredient, alone or together with other substances toxic to arthropods and plant nematodes. The actual compositions employed and their rate of application will be selected to achieve the desired effect(s) by the farmer, livestock producer, medical or veterinary practitioner, pest control operator or other person skilled in the art. For example, solid and liquid compositions for application topically to animals, timber, stored products or household goods usually contain from 0.00005% to 90%, more particularly from 0.001% to 10%, by weight of one or more of the active ingredient. For administration to animals orally or parenterally, including percutaneously solid and liquid compositions normally contain from 0.1% to 90% by weight of one or more of the active ingredient. Medicated feedstuffs normally contain from 0.001% to 3% of one or more of the active ingredient. Concentrates and supplements for mixing with feedstuffs normally contain from 5% to 90%, and preferably from 5% to 50%, by weight of one or more of the active ingredient. Mineral salt licks normally contain from 0.1% to 10% by weight of one or more of the active ingredient. Dusts and liquid compositions for application to livestock, persons, goods, premises or outdoor areas may contain 0.0001% to 15%, and more especially 0.005% to 2.0%, by weight of one or more of the active ingredient. Suitable concentrations in treated waters are between 0.0001 ppm and 20 ppm, and more especially 0.001 ppm to 5.0 ppm. of one or more of the active ingredient and may also be used therapeutically in fish farming with appropriate exposure times. Edible baits may contain from 0.01% to 5% and preferably 0.01% to 1.0%, by weight of one or more of the active ingredient.

When administered to vertebrates parenterally, orally or by percutaneous or other means, the dosage of the active ingredient will depend upon the species, age and health of the vertebrate and upon the nature and degree of its actual or potential infestation by arthropod, helminth or protozoan pest. A single dose of 0.1 to 100 mg, preferably 2.0 to 20.0 mg, per kg body weight of the animal or doses of 0.01 to 20.0 mg, preferably 0.1 to 5.0 mg, per kg body weight of the animal per day for sustained medication are generally suitable by oral or parenteral administration. By use of sustained release formulations or devices, the daily doses required over a period of months may be combined and administered to animals on a single occasion.

The following examples are presented in order to more fully illustrate certain embodiments of the invention. They should in no way, however, be construed as limiting the broad scope of the invention. One skilled in the art can readily devise many variations and modifications of the principles disclosed herein without departing from the spirit and scope of the invention.

EXPERIMENTAL DETAILS SECTION

Example 1

Preparation of Amorphous Fipronil 5 g. of fipronil (97%) were placed in flask and heated up to 215° C. (above the melting point). The liquid magma was held at that temperature for 45 minutes and afterwards was placed in cold iced bath to form the amorphous solid.

X-ray powder diffraction pattern (FIG. 15) shows no significant signals, thus indicating an amorphous Fipronil solid.

Example 2

Preparation of Fipronil Form I and Fipronil Form III

Fipronil Form I is formed by heating and grinding fipronil pseudomorph F-ST up to ~150° C. for a few minutes. An intermediate in the conversion of pseudomorph FS-T to Form I is a novel polymorphic fipronil Form III. As a result of heating FS-T, solvent liberation occurs resulting in the formation of Form III, which then undergoes exothermic transition to Form I.

Example 3

Preparation of Fipronil Form II 3.1 Crystallization from Isopropanol 2 g. of fipronil was dissolved in 10 g. of isopropyl alcohol at 82° C. The resulting clear solution was slowly cooled to RT and then placed in ice/water bath for an hour. White crystal line solid appeared and was filtered over filter paper. The resulting solid was dried at 40° C. in the oven.

mp of the crystals: 195° C. (at 2° C. or 10° C./min).
IR bands: 3436.5 and 3344 $cm^{-1}$ 3.2 Crystallization from n-Hexane-Ethyl Acetate Slurry of 2 g. of fipronil and 90 g. of n-hexane was heated up to 69° C. Ethyl acetate was added dropwise until a clear solution was obtained (total of 71 g.). The solution was then cooled under agitation to room temperature. White crystals obtained in the bottom of the flask. The crystals were filtered and then dried at 40° C.

mp=196° C. (at 2° C. or 10° C./min).
IR bands: 3436.5 and 3344 $cm^{-1}$ 3.3 Crystallization from n-Hexane-Methyl Isobutyl Ketone (MIBK)

A solution of 3 g. fipronil and 10 g. of MIBK was heated to 95° C. At that temperature 17.5 g. of n-hexane were added dropwise. The mixture was cooled at room temperature and then placed in ice/water bath. White crystals were filtered out and then dried at 40° C.

mp=196° C. (at 2° C. or 10° C./min)
IR bands: 3436.5 and 3344 $cm^{-1}$ 3.4 Crystallization from 1-propanol 3 g. of fipronil and 40 g. of 1-propanol were heated to reflux. The solution held at reflux for 30 minutes and was cooled to room temperature without stirring. Crystals appeared after 2 days and filtered with vacuum. The crystals were dried at 80° C. overnight. The resulting crystals were fipronil Form II.

3.5 Crystallization from Butanol

Fipronil was crystallized from butanol as described above in Example 3.4, (ratio of 4 g. fipronil to 40 g. of Butanol) resulting in fipronil Form II.

Example 4

Preparation of Fipronil Pseudomorph

Toluene Hemi-Solvate (F-ST)

2 g. of Fipronil and 10 g. of toluene were heated up to 110° C. until full dissolution. White crystals appeared within the cooling process to RT. The crystals were filtered and then dried at 40° C. Toluene solvate detected by TGA (weight loss) and identified via solid state IR measurement (peaks at 694.6 and 733.2 $cm^{-1}$)

IR bands: 3409.5 and 3328.4 $cm^{-1}$

Example 5

Preparation of Fipronil Pseudomorph

MIBK Hemi-Solvate (F-SM)

2 g. of Fipronil and 10 g. of MIBK (methyl isobutyl ketone) were dissolved at RT. At 100° C. 15.4 g. of n-hexane were added dropwise. White crystalline powder appeared over the flask walls after 12 days at RT while it was left open, and the n-hexane was evaporated from it slowly. The solid was collected from the flask and dried at 40° C. MIBK solvate detected by TGA (weight loss) and identified via solid state IR measurement (peak at 1710 $cm^{-1}$)

IR bands: 3409.5 and 3328.4 $cm^{-1}$

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

The invention claimed is:

1. A form of 5-amino-1-[2,6-dichloro-4-(trifluoromethyl) phenyl]-4-[(trifluoromethyl)sulfinyl]-1H-pyrazole-3-carbonitrile which is crystalline polymorph Form I which exhibits at least one of the following properties:
   (a) an X-ray powder diffraction pattern having characteristic peaks expressed in degrees 2θ (+/−0.20°θ) at about 13.04, 16.27, 18.48, 19.65, 22.05, and 31.55;
   (b) an X-ray powder diffraction pattern having characteristic peaks expressed in degrees 2θ (+/−0.20°θ) at about 10.3, 11.05, 13.04, 15.93, 16.27, 18.48, 19.65, 20.34, 22.05, and 31.55, substantially as shown in FIG. 1; or
   (c) an infrared (IR) spectrum at the 3000 $cm^{-1}$ range, having characteristic peaks at about 3332 and 3456 $cm^{-1}$, substantially as shown in FIG. 2.

2. The crystalline polymorph Form I of claim 1 in a mixture with 5-amino-1-[2,6-dichloro-4-(trifluoromethyl)phenyl]-4-[(trifluoromethyl)sulfinyl]-1H-pyrazole-3-carbonitrile which is crystalline polymorph Form II which exhibits at least one of the following properties:
   (a) an X-ray powder diffraction pattern having characteristic peaks expressed in degrees 2θ (+/−0.20°θ) at about 14.4, 15.7, 16.75, 17.2, 19, 20.7, 22.95, 23.55, and 32.15;
   (b) an infrared (IR) spectrum at the 3000 $cm^{-1}$, having characteristic peaks at about 3344 and 3436.5 $cm^{-1}$;
   (c) a Differential Scanning Calorimeter (DSC) thermogram having a single predominant endotherm at about 195° C. as measured by a Differential Scanning Calorimeter (DSC) at a scan rate of 2° C. or 10° C. per minute.

3. The mixture claim 2 comprising about 10-90% by weight of polymorphic Form I and about 90% to about 10% by weight of polymorphic Form II.

4. A process for the preparation of the polymorph Form I of claim 1, the process comprising the steps of heating a 5-amino-1-[2,6-dichloro-4-(trifluoromethyl)phenyl]-4-[(trifluoromethyl)sulfinyl]-IH-pyrazole-3-carbonitrile toluene hemi solvate (FS-T) pseudomorph to a temperature greater than about 100° C.; cooling; and isolating the product.

5. The process according to claim 4, wherein the temperature is about 150° C.

6. A pesticidal composition comprising:
   (a) a pesticidally effective amount of a solid crystal compound according to claim 1; and
   (b) a pesticidally acceptable adjuvant.

7. The pesticidal composition according to claim 6, in a form and amount effective for use in veterinary medicine, agriculture, treating fields or crops, household pest control, or roach, ant or termite control.

8. The pesticidal composition according to claim 6, in a form suitable for percutaneous administration or topical administration.

9. The pesticidal composition according to claim 6, in a form suitable for a spray, pest bait, granules, a gel or a suspension.

10. A method for controlling pests at a locus, said method comprising applying to said locus a pesticidally effective amount of a composition according to claim 6.

11. The crystalline polymorph Form I of claim 1, wherein the polymorph exhibits a Differential Scanning Calorimeter (DSC) thermogram having a single predominant endotherm at about 202.5° C. as measured by a Differential Scanning Calorimeter (DSC) at a scan rate of 2° C. and/or 10° C. per minute.

12. The crystalline polymorph Form I of claim 11, substantially as shown in FIG. 3.

13. A pesticidal composition comprising:
   (a) a pesticidally effective amount of a solid crystal compound mixture according to claim 2; and
   (b) a pesticidally acceptable adjuvant.

14. The pesticidal composition according to claim 13, in a form and amount effective for use in veterinary medicine, agriculture, treating fields or crops, household pest control, or roach, ant or termite control.

15. The pesticidal composition according to claim 13, in a form suitable for percutaneous administration or topical administration.

16. The pesticidal composition according to claim 13, in a form suitable for a spray, pest bait, granules, a gel or a suspension.

17. A method for controlling pests at a locus, said method comprising applying to said locus a pesticidally effective amount of a composition according to claim 13.

* * * * *

UNITED STATES PATENT AND TRADEMARK OFFICE
CERTIFICATE OF CORRECTION

PATENT NO.       : 8,440,709 B2
APPLICATION NO.  : 12/097615
DATED            : May 14, 2013
INVENTOR(S)      : Sharona Zamir Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 986 days.

Signed and Sealed this
Eighth Day of September, 2015

Michelle K. Lee
*Director of the United States Patent and Trademark Office*